United States Patent
Hirokawa

(10) Patent No.: US 12,361,590 B2
(45) Date of Patent: Jul. 15, 2025

(54) IMAGE PROCESSING METHOD, IMAGE PROCESSING DEVICE, AND PROGRAM

(71) Applicant: NIKON CORPORATION, Tokyo (JP)

(72) Inventor: Mariko Hirokawa, Yokohama (JP)

(73) Assignee: NIKON CORPORATION, Tokyo (JP)

(*) Notice: Subject to any disclaimer, the term of this patent is extended or adjusted under 35 U.S.C. 154(b) by 475 days.

(21) Appl. No.: 17/782,093

(22) PCT Filed: Nov. 12, 2020

(86) PCT No.: PCT/JP2020/042252
§ 371 (c)(1),
(2) Date: Jun. 2, 2022

(87) PCT Pub. No.: WO2021/111840
PCT Pub. Date: Jun. 10, 2021

(65) Prior Publication Data
US 2023/0010672 A1    Jan. 12, 2023

(30) Foreign Application Priority Data
Dec. 5, 2019  (JP) ................. 2019-220285

(51) Int. Cl.
G06F 17/00   (2019.01)
A61B 3/12   (2006.01)
G06T 7/00   (2017.01)
G06T 7/73   (2017.01)
A61B 3/10   (2006.01)

(52) U.S. Cl.
CPC ............ *G06T 7/75* (2017.01); *A61B 3/1225* (2013.01); *G06T 7/0012* (2013.01); *A61B 3/102* (2013.01); *G06T 2207/10101* (2013.01); *G06T 2207/30041* (2013.01); *G06T 2207/30101* (2013.01)

(58) Field of Classification Search
CPC ............... G06T 7/75; G06T 7/0012; G06T 2207/10101; G06T 2207/30041; G06T 2207/30101; A61B 3/1225; A61B 3/102
See application file for complete search history.

(56) References Cited

U.S. PATENT DOCUMENTS

| | | | |
|---|---|---|---|
| 2013/0295014 A1* | 11/2013 | Boyd | A61K 9/0048 424/9.2 |
| 2014/0118690 A1* | 5/2014 | Sato | G01B 9/02091 351/206 |
| 2016/0128561 A1* | 5/2016 | Terasaki | A61B 3/152 351/221 |
| 2017/0127937 A1* | 5/2017 | Fujii | G01B 9/02091 |

(Continued)

FOREIGN PATENT DOCUMENTS

JP    7306482 B2    7/2023

OTHER PUBLICATIONS

Ohno-Matsui et al, "The long-term follow-up of a highly myopic patient with a macular vortex vein", Department of Opthamology and Radiology, School of Medicine, 4 pages. (Year: 1997).*

(Continued)

*Primary Examiner* — Mohammed H Zuberi
(74) *Attorney, Agent, or Firm* — Foley & Lardner LLP

(57) ABSTRACT

An image processing method performed by a processor and including detecting positions of plural vortex veins in a fundus image of an examined eye, and computing a center of distribution of the plural detected vortex vein positions.

17 Claims, 19 Drawing Sheets

(56) References Cited

U.S. PATENT DOCUMENTS

| | | | |
|---|---|---|---|
| 2018/0279877 A1* | 10/2018 | Berdahl | A61B 3/1241 |
| 2020/0394789 A1* | 12/2020 | Freund | G06T 7/0012 |
| 2021/0004939 A1* | 1/2021 | Hirokawa | A61B 3/0025 |
| 2021/0035294 A1* | 2/2021 | Tanabe | A61B 3/0025 |

OTHER PUBLICATIONS

Japanese Office Action issued in corresponding JP Appl. Ser. No. 2024-020353 Dated Jan. 21, 2025 (3 pages).

\* cited by examiner

FIG.16

| ID | EYE AXIAL LENGTH (mm) | TYPE | DISTANCE (mm) | ANGLE (deg) | LONGITUDE (deg) | LATITUDE (deg) | LONGITUDINAL DISTANCE (mm) | LATITUDINAL DISTANCE (mm) |
|---|---|---|---|---|---|---|---|---|
| 123456 | 24 | VV CENTER | | | | | | |
| | | VV1 | | | | | | |
| | | VV2 | | | | | | |
| | | VV3 | | | | | | |
| | | VV4 | | | | | | |
| | | ... | | | | | | |

FIG.18

IMAGE PROCESSING METHOD, IMAGE PROCESSING DEVICE, AND PROGRAM

TECHNICAL FIELD

Technology disclosed herein relates to an image processing method, an image processing device, and a program.

BACKGROUND ART

There is a desire to be able to analyze vortex veins in fundus images (specification of U.S. Pat. No. 8636364).

SUMMARY OF INVENTION

An image processing method of a first aspect of technology disclosed herein is an image processing method performed by a processor and including detecting positions of plural vortex veins in a fundus image of an examined eye, and computing a center of distribution of the detected plural vortex vein positions.

An image processing device of a second aspect of technology disclosed herein includes memory and a processor connected to the memory wherein the processor is configured to detect positions of plural vortex veins in a fundus image of an examined eye, and compute a center of distribution of the detected plural vortex vein positions.

A program of a third aspect of technology disclosed herein causes a computer to execute processing including detecting positions of plural vortex veins in a fundus image of an examined eye, and computing a center of distribution of the detected plural vortex vein positions.

BRIEF DESCRIPTION OF DRAWINGS

FIG. 16 illustrates a feature value table stored with feature values indicating positional relationships between an optic nerve head ONH and VV center.

FIG. 18 is a diagram illustrating a second display screen 300B for displaying targets and feature values.

DESCRIPTION OF EMBODIMENTS

Detailed explanation follows regarding an exemplary embodiment of technology disclosed herein, with reference to the drawings.

Figure 1:
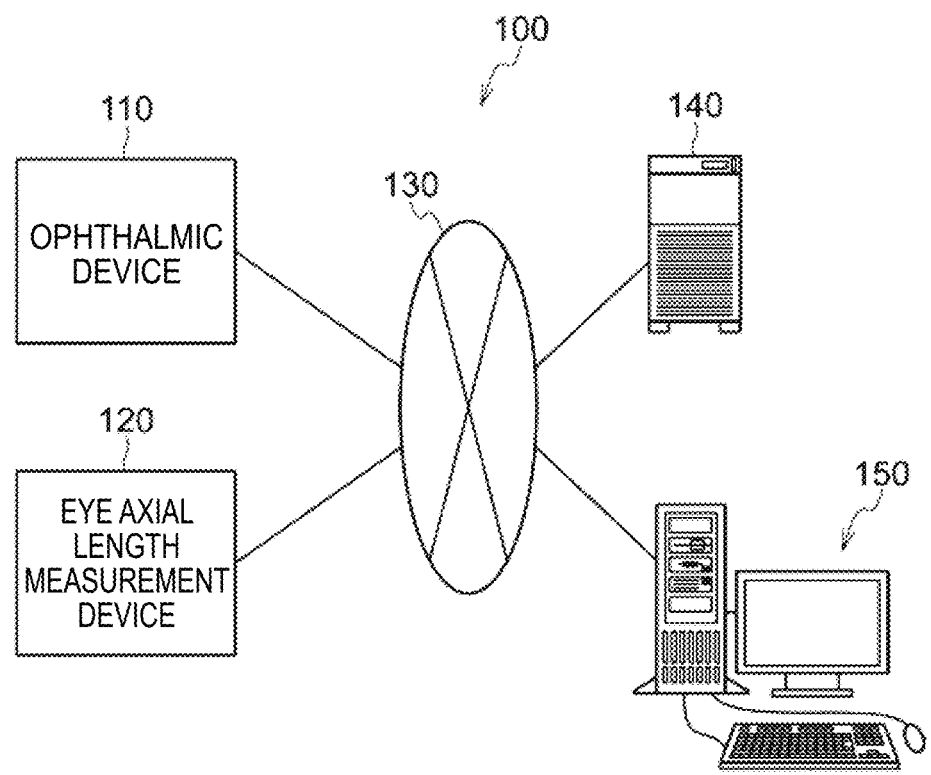
FIG. 1 is a block diagram of an ophthalmic system 100.

Explanation follows regarding a configuration of an ophthalmic system 100, with reference to FIG. 1. As illustrated in FIG. 1, the ophthalmic system 100 includes an ophthalmic device 110, an eye axial length measurement device 120, a management server device (referred to hereafter as "server") 140, and an image display device (referred to hereafter as "viewer") 150. The ophthalmic device 110 acquires an image of a fundus. The eye axial length measurement device 120 measures the axial length of the eye of a patient. The server 140 stores fundus images that were obtained by imaging the fundus of patients using the ophthalmic device 110 in association with patient IDs. The viewer 150 displays medical information such as fundus images acquired from the server 140.

The ophthalmic device 110, the eye axial length measurement device 120, the server 140, and the viewer 150 are connected together through a network 130.

Figure 2:
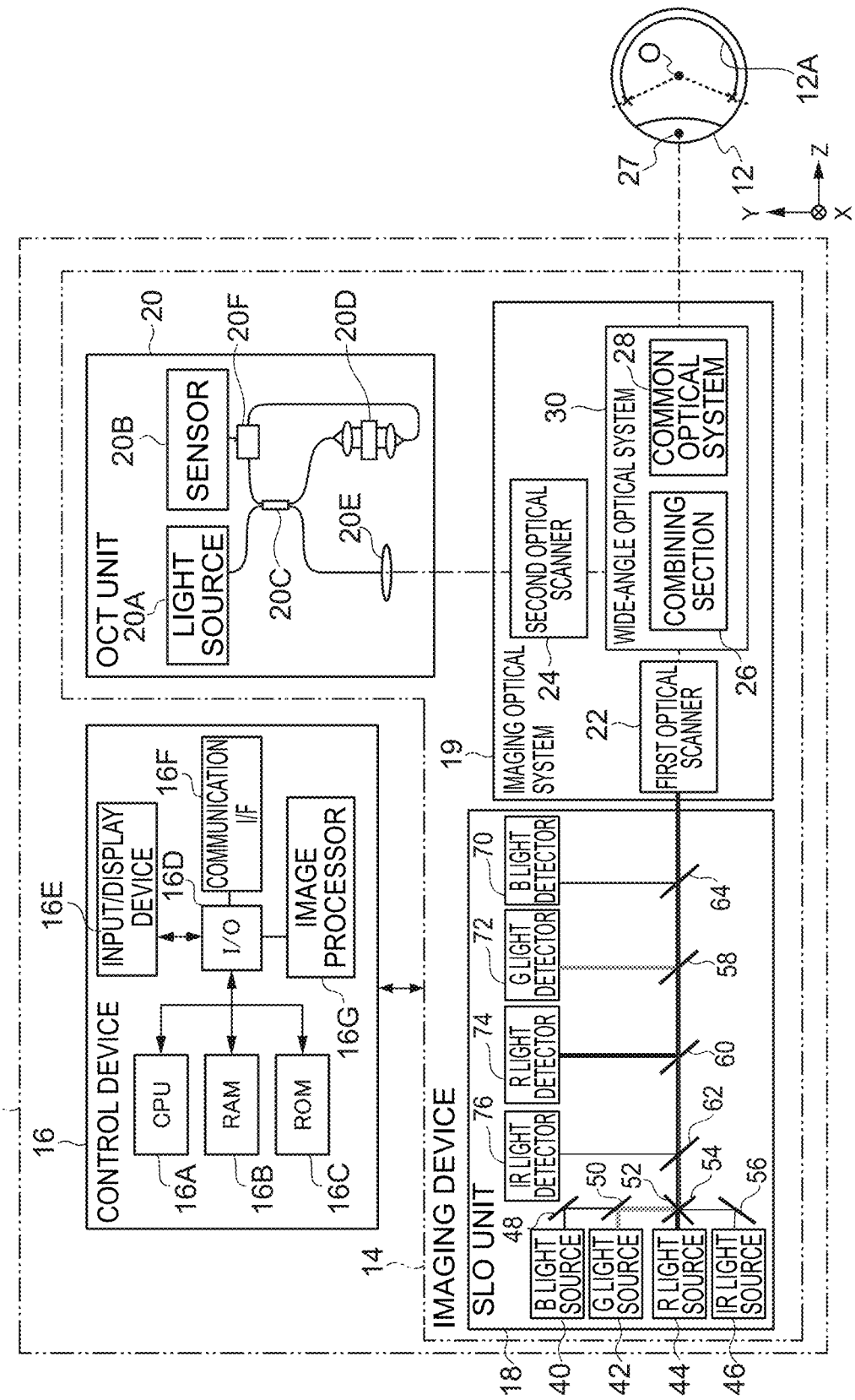
FIG. 2 is a schematic configuration diagram illustrating an overall configuration of an ophthalmic device 110.

Next, explanation follows regarding a configuration of the ophthalmic device 110, with reference to FIG. 2.

For ease of explanation, scanning laser ophthalmoscope is abbreviated to SLO. Optical coherence tomography is also abbreviated to OCT.

With the ophthalmic device 110 installed on a horizontal plane and a horizontal direction taken as an X direction, a direction perpendicular to the horizontal plane is denoted a Y direction, and a direction connecting the center of the pupil at the anterior eye portion of the examined eye 12 and the center of the eyeball is denoted a Z direction. The X direction, the Y direction, and the Z direction are thus mutually perpendicular directions.

The ophthalmic device 110 includes an imaging device 14 and a control device 16. The imaging device 14 is provided with an SLO unit 18, an OCT unit 20, and an imaging optical system 19, and acquires a fundus image of the fundus of the examined eye 12. Two-dimensional fundus images that have been acquired by the SLO unit 18 are referred to hereafter as SLO images. Tomographic images, face-on images (enface images) and the like of the retina created based on OCT data acquired by the OCT unit 20 are referred to hereafter as OCT images.

The control device 16 includes a computer provided with a Central Processing Unit (CPU) 16A, Random Access Memory (RAM) 16B, Read-Only Memory (ROM) 16C, and an input/output (I/O) port 16D.

The control device 16 is provided with an input/display device 16E connected to the CPU 16A through the I/O port 16D. The input/display device 16E includes a graphical user interface to display images of the examined eye 12 and to receive various instructions from a user. An example of the graphical user interface is a touch panel display.

The control device 16 is provided with an image processor 16G connected to the I/O port 16D. The image processor 16G generates images of the examined eye 12 based on data acquired by the imaging device 14. Note that the image processor 16G may be omitted, and the CPU 16A generate images of the examined eye 12 based on data obtained by the imaging device 14. The control device 16 is provided with a communication interface (I/F) 16F connected to the I/O port 16D. The ophthalmic device 110 is connected to the eye axial length measurement device 120, the server 140, and the viewer 150 through the communication interface (I/F) 16F and the network 130.

Although the control device 16 of the ophthalmic device 110 is provided with the input/display device 16E as illustrated in FIG. 2, the technology disclosed herein is not limited thereto. For example, a configuration may adopted in which the control device 16 of the ophthalmic device 110 is not provided with the input/display device 16E, and instead a separate input/display device is provided that is physically independent of the ophthalmic device 110. In such cases, the display device is provided with an image processing processor unit that operates under the control of the CPU 16A in the control device 16. Such an image processing processor unit may display SLO images and the like based on an image signal output as an instruction by the CPU 16A.

The imaging device 14 operates under the control of the CPU 16A of the control device 16. The imaging device 14 includes the SLO unit 18, the imaging optical system 19, and the OCT unit 20. The imaging optical system 19 includes a first optical scanner 22, a second optical scanner 24, and a wide-angle optical system 30.

The first optical scanner 22 scans light emitted from the SLO unit 18 two dimensionally in the X direction and the Y direction. The second optical scanner 24 scans light emitted from the OCT unit 20 two dimensionally in the X direction and the Y direction. As long as the first optical scanner 22 and the second optical scanner 24 are optical elements capable of deflecting light beams, they may be configured by any out of, for example, polygon mirrors, mirror galvanometers, or the like. A combination thereof may also be employed.

The wide-angle optical system 30 includes an objective optical system (not illustrated in FIG. 2) provided with a common optical system 28, and a combining section 26 that combines light from the SLO unit 18 with light from the OCT unit 20.

The objective optical system of the common optical system 28 may be a reflection optical system employing a concave mirror such as an elliptical mirror, a refraction optical system employing a wide-angle lens, or may be a reflection-refraction optical system employing a combination of a concave mirror and a lens. Employing a wide-angle optical system that utilizes an elliptical mirror, wide-angle lens, or the like enables imaging to be performed not only of a central portion of the fundus where the optic nerve head and macula are present, but also of the retina at a fundus peripheral portion where an equatorial portion of the eyeball and vortex veins are present.

For a system including an elliptical mirror, a configuration may be adopted that utilizes an elliptical mirror system as disclosed in International Publication (WO) Nos. 2016/103484 or 2016/103489. The disclosures of WO Nos. 2016/103484 and 2016/103489 are incorporated in their entirety by reference herein.

Observation of the fundus over a wide field of view (FOV) 12A is implemented by employing the wide-angle optical system 30. The FOV 12A refers to a range capable of being imaged by the imaging device 14. The FOV 12A may be expressed as a viewing angle. In the present exemplary embodiment the viewing angle may be defined in terms of an internal illumination angle and an external illumination angle. The external illumination angle is the angle of illumination by a light beam shone from the ophthalmic device 110 toward the examined eye 12, and is an angle of illumination defined with reference to a pupil 27. The internal illumination angle is the angle of illumination of a light beam shone onto the fundus, and is an angle of illumination defined with reference to an eyeball center O. A correspondence relationship exists between the external illumination angle and the internal illumination angle. For example, an external illumination angle of 120° is equivalent to an internal illumination angle of approximately 160°. The internal illumination angle in the present exemplary embodiment is 200°.

An angle of 200° for the internal illumination angle is an example of a "specific value" of technology disclosed herein.

SLO fundus images obtained by imaging at an imaging angle having an internal illumination angle of 160° or greater are referred to as UWF-SLO fundus images. UWF is an abbreviation of ultra-wide field. Obviously an SLO image that is not UWF can be acquired by imaging the fundus at an imaging angle that is an internal illumination angle of less than 160°.

An SLO system is realized by the control device 16, the SLO unit 18, and the imaging optical system 19 as illustrated in FIG. 2. The SLO system is provided with the wide-angle optical system 30, enabling fundus imaging over the wide FOV 12A, and specifically enabling imaging of a region spanning from a posterior pole portion of the fundus of the examined eye 12 and extending past an equatorial portion.

Figure 3A:
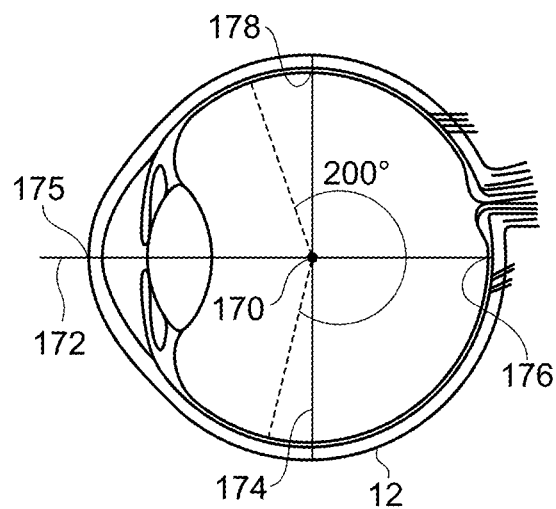
FIG. 3A is a first diagram illustrating an imaging range on a fundus of an examined eye 12 by the ophthalmic device 110.

Explanation follows regarding an equatorial portion 178 with reference to FIG. 3A. The eyeball (the examined eye 12) is a spherical structure having an eyeball center 170 and a diameter of about 24 mm. A straight line connecting an anterior pole 175 thereof with a posterior pole 176 thereof is called an ocular axis 172, a line running along an intersection between a plane orthogonal to the ocular axis 172 and the eyeball surface is referred to as a line of latitude, and the equator 174 corresponds to the line of latitude with the greatest length. Portions of the retina and the choroid coinciding with the position of the equator 174 configure an equatorial portion 178. The equatorial portion 178 is one part of a fundus peripheral portion.

The ophthalmic device 110 is capable of imaging a region covered by an internal illumination angle of 200° with respect to a reference position that is the eyeball center 170 of the examined eye 12. Note that an internal illumination angle of 200° corresponds to an external illumination angle of 167° with reference to the pupil of the eyeball of the examined eye 12. Namely, the wide-angle optical system 80 illuminates laser light through the pupil at an angle of view corresponding to an external illumination angle of 167° in order to image a fundus region over an internal illumination angle of 200°.

Figure 3B:
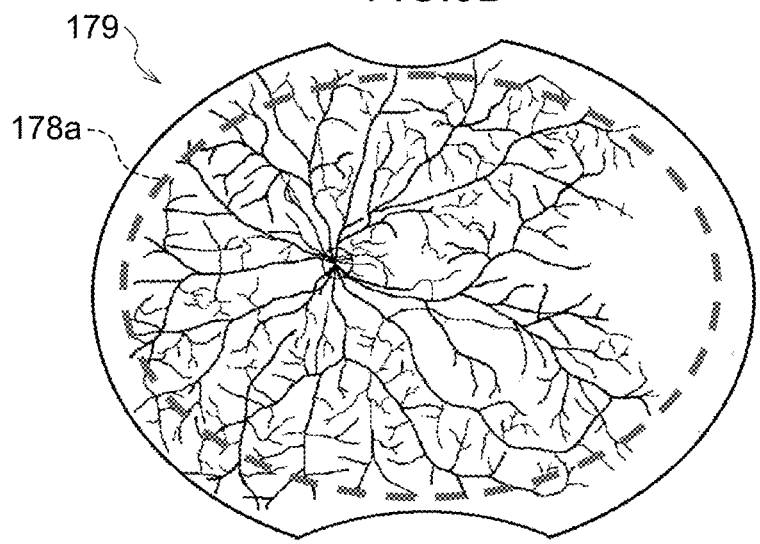
FIG. 3B is a second diagram illustrating an imaging range on a fundus of an examined eye 12 by an ophthalmic device 110, and is an image of a fundus obtained by such imaging.

FIG. 3B illustrates an SLO image 179 obtained by imaging with the ophthalmic device 110 capable of scanning with an internal illumination angle of 200°. As illustrated in FIG. 3B, the equatorial portion 178 corresponds to an internal illumination angle of 180°, and the location indicated by the dotted line 178a in the SLO image 179 corresponds to the equatorial portion 178. In this manner, the ophthalmic device 110 is capable of imaging a fundus peripheral area spanning from a posterior pole portion including the posterior pole 176 and extending past the equatorial portion 178 in a single take (either a single image or a single scan). Namely, the ophthalmic device 110 is capable of capturing from a central portion of the fundus to a peripheral portion of the fundus in a single take.

Figure 3C:
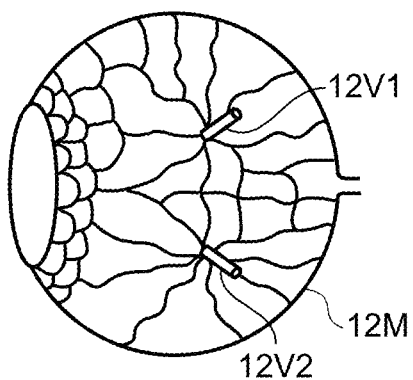
FIG. 3C is a third diagram illustrating an imaging range on a fundus of an examined eye 12 by an ophthalmic device 110.

FIG. 3C is a diagram illustrating a positional relationship between a choroid 12M and vortex veins 12V1, 12V2 of the eyeball, as described in detail later.

In FIG. 3C, choroidal blood vessels of the choroid 12M are illustrated in a mesh pattern. The choroidal blood vessels carry blood around the entire choroid. Blood flows out from the eyeball through plural vortex veins present in the examined eye 12. FIG. 3C illustrates an upper vortex vein V1 and a lower vortex vein V2 present on one side of the eyeball. Vortex veins are frequently present in the vicinity of the equatorial portion 178. Accordingly, the ophthalmic device 110 that is capable of scanning the fundus peripheral portion over a broad range with an internal illumination angle of 200° as described above is employed in order to image the vortex veins and the choroidal blood vessels peripheral to the vortex veins that are present in the examined eye 12.

The configuration of the ophthalmic device 110 provided with the wide-angle optical system 30 as described above may employ the configuration described in International Application No. PCT/EP 2017/075852. The disclosure of International Application No. PCT/EP 2017/075852 (WO No. 2018/069346), filed internationally on Oct. 10, 2017, is incorporated in its entirety by reference herein.

Returning to FIG. 2, the SLO unit 18 is provided with plural light sources such as, for example, a blue (B) light source 40, a green (G) light source 42, a red (R) light source 44, an infrared (for example near infrared) (IR) light source 46, and optical systems 48, 50, 52, 54, 56 to guide the light from the light sources 40, 42, 44, 46 onto a single optical path using reflection or transmission. The optical systems 48, 50, 56 are configured by mirrors, and the optical systems 52, 54 are configured by beam splitters. B light is reflected by the optical system 48, is transmitted through the optical system 50, and is reflected by the optical system 54. G light is reflected by the optical systems 50, 54, R light is transmitted through the optical systems 52, 54, and IR light is reflected by the optical systems 56, 52. The respective lights are thereby guided onto a single optical path.

The SLO unit 18 is configured so as to be capable of switching between the light source or the combination of light sources employed for emitting laser light of different wavelengths, such as a mode in which G light, R light and B light are emitted, a mode in which infrared light is emitted, etc. Although the example in FIG. 2 includes four light sources, i.e. the B light source 40, the G light source 42, the R light source 44, and the IR light source 46, the technology disclosed herein is not limited thereto. For example, the SLO unit 18 may, furthermore, also include a white light source, in a configuration in which light is emitted in various modes, such as a mode in which white light is emitted alone.

Light introduced to the imaging optical system 19 from the SLO unit 18 is scanned in the X direction and the Y direction by the first optical scanner 22. The scanning light passes through the wide-angle optical system 30 and the pupil 27 and is shone onto the posterior eye portion of the examined eye 12. Reflected light that has been reflected by the fundus passes through the wide-angle optical system 30 and the first optical scanner 22 and is introduced into the SLO unit 18.

The SLO unit 18 is provided with a beam splitter 64 that, from out of the light coming from the posterior eye portion (e.g. fundus) of the examined eye 12, reflects the B light therein and transmits light other than B light therein, and a beam splitter 58 that, from out of the light transmitted by the beam splitter 64, reflects the G light therein and transmits light other than G light therein. The SLO unit 18 is further provided with a beam splitter 60 that, from out of the light transmitted through the beam splitter 58, reflects R light therein and transmits light other than R light therein. The SLO unit 18 is further provided with a beam splitter 62 that reflects IR light from out of the light transmitted through the beam splitter 60.

The SLO unit 18 is provided with plural light detectors corresponding to the plural light sources. The SLO unit 18 includes a B light detector 70 for detecting B light reflected by the beam splitter 64, and a G light detector 72 for detecting G light reflected by the beam splitter 58. The SLO unit 18 includes an R light detector 74 for detecting R light reflected by the beam splitter 60, and an IR light detector 76 for detecting IR light reflected by the beam splitter 62.

Light that has passed through the wide-angle optical system 30 and the first optical scanner 22 and been introduced into the SLO unit 18 (i.e. reflected light that has been reflected by the fundus) is reflected by the beam splitter 64 and photo-detected by the B light detector 70 when B light, and is transmitted through the beam splitter 64, reflected by the beam splitter 58, and photo-detected by the G light detector 72 when G light. When R light, the incident light is transmitted through the beam splitters 64, 58, reflected by the beam splitter 60, and photo-detected by the R light detector 74. When IR light, the incident light is transmitted through the beam splitters 64, 58, 60, reflected by the beam splitter 62, and photo-detected by the IR light detector 76.

The image processor 16G that operates under the control of the CPU 16A employs signals detected by the B light detector 70, the G light detector 72, the R light detector 74, and the IR light detector 76 to generate UWF-SLO images.

The UWF-SLO image (also sometimes referred to as a UWF fundus image or an original image as described below) encompasses a UWF-SLO image (green fundus image) obtained by imaging the fundus in green, and a UWF-SLO image (red fundus image) obtained by imaging the fundus in red. The UWF-SLO image further encompasses a UWF-SLO image (blue fundus image) obtained by imaging the fundus in blue, and a UWF-SLO image (IR fundus image) obtained by imaging the fundus in IR.

The control device 16 also controls the light sources 40, 42, 44 so as to emit light at the same time. A green fundus image, a red fundus image, and a blue fundus image are obtained with mutually corresponding positions by imaging the fundus of the examined eye 12 at the same time with the B light, G light, and R light. An RGB color fundus image is obtained from the green fundus image, the red fundus image, and the blue fundus image. The control device 16 obtains a green fundus image and a red fundus image with mutually corresponding positions by controlling the light sources 42, 44 so as to emit light at the same time and to image the fundus of the examined eye 12 at the same time with the G light and R light. A RG color fundus image is obtained from the green fundus image and the red fundus image.

Specific examples of the UWF-SLO image include a blue fundus image, a green fundus image, a red fundus image, an IR fundus image, an RGB color fundus image, and an RG color fundus image. The image data for the respective UWF-SLO images are transmitted from the ophthalmic device 110 to the server 140 through the communication interface (I/F) 16F, together with patient information input through the input/display device 16E. The image data of the respective UWF-SLO images and the patient information is stored associated with each other in memory 164. The patient information includes, for example, patient ID, name, age, visual acuity, right eye/left eye discriminator, and the like. The patient information is input by an operator through the input/display device 16E.

An OCT system is realized by the control device 16, the OCT unit 20, and the imaging optical system 19 illustrated in FIG. 2. The OCT system is provided with the wide-angle optical system 30. This enables fundus imaging to be performed over the wide FOV 12A similarly to when imaging the SLO fundus images as described above. The OCT unit 20 includes a light source 20A, a sensor (detector) 20B, a first light coupler 20C, a reference optical system 20D, a collimator lens 20E, and a second light coupler 20F.

Light emitted from the light source 20A is split by the first light coupler 20C. After one part of the split light has been collimated by the collimator lens 20E into parallel light, to serve as measurement light, the parallel light is introduced into the imaging optical system 19. The measurement light is scanned in the X direction and the Y direction by the second optical scanner 24. The scanning light is shone onto the fundus through the wide-angle optical system 30 and the pupil 27. Measurement light that has been reflected by the fundus passes through the wide-angle optical system 30 and the second optical scanner 24 so as to be introduced into the OCT unit 20. The measurement light then passes through the collimator lens 20E and the first light coupler 20C before being incident to the second light coupler 20F.

The other part of the light emitted from the light source 20A and split by the first light coupler 20C is introduced into the reference optical system 20D as reference light, and is made incident to the second light coupler 20F through the reference optical system 20D.

The respective lights that are incident to the second light coupler 20F, namely the measurement light reflected by the fundus and the reference light, interfere with each other in the second light coupler 20F so as to generate interference light. The interference light is photo-detected by the sensor 20B. The image processor 16G operating under the control of the CPU 16A generates OCT images, such as tomographic images and en-face images, based on OCT data detected by the sensor 20B. Note that the image processor 16G may be omitted, and the CPU 16A may generate OCT images based on OCT data detected by the sensor 20B.

OCT fundus images obtained by imaging at an imaging angle having an internal illumination angle of 160° or greater are referred to as UWF-OCT images. Obviously OCT fundus image data can be acquired at an imaging angle having an internal illumination angle of less than 160°.

The image data of the UWF-OCT images is transmitted, together with the patient information, from the ophthalmic device 110 to the server 140 though the communication interface (I/F) 16F. The image data of the UWF-OCT images and the patient information are stored associated with each other in the memory 164.

Note that although in the present exemplary embodiment an example is given in which the light source 20A is a wavelength swept-source OCT (SS-OCT), the light source 20A may be configured from various types of OCT system, such as a spectral-domain OCT (SD-OCT) or a time-domain OCT (TD-OCT) system.

Next, explanation follows regarding the eye axial length measurement device 120. The eye axial length measurement device 120 has two modes, i.e. a first mode and a second mode, for measuring eye axial length, this being the length of an examined eye 12 in an eye axial direction. In the first mode light from a non-illustrated light source is guided into the examined eye 12. Interference light between light reflected from the fundus and light reflected from the cornea is photo-detected, and the eye axial length is measured based on an interference signal representing the photo-detected interference light. The second mode is a mode to measure the eye axial length by employing non-illustrated ultrasound waves.

The eye axial length measurement device 120 transmits the eye axial length as measured using either the first mode or the second mode to the server 140. The eye axial length may be measured using both the first mode and the second mode, and in such cases, an average of the eye axial lengths as measured using the two modes is transmitted to the server 140 as the eye axial length. The server 140 stores the eye axial length of the patients in association with the patient ID.

Figure 4:
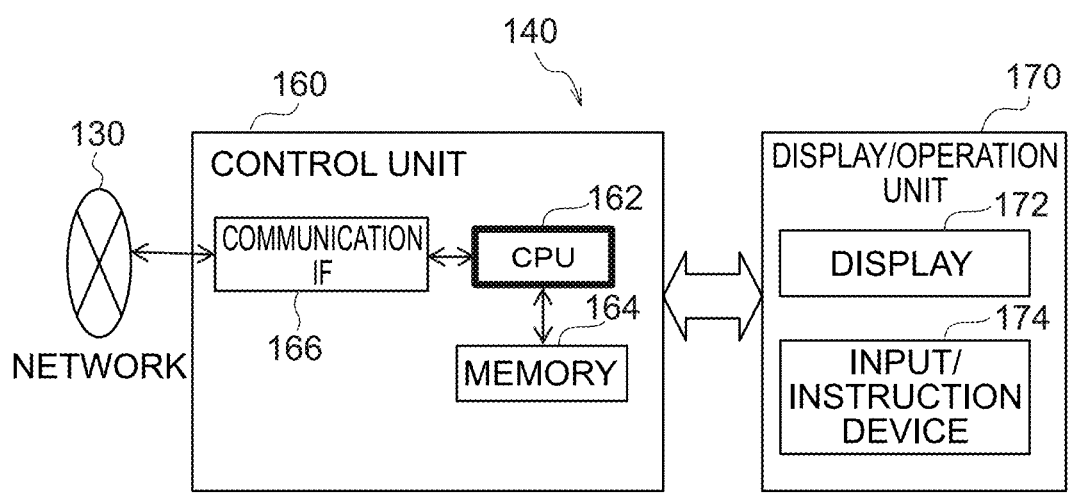
FIG. 4 is a block diagram illustrating a configuration of a server 140.

Next, a configuration of the server 140 will be described with reference to FIG. 4. As illustrated in FIG. 4, the server 140 includes a control unit 160, and a display/operation unit 170. The control unit 160 is equipped with a computer including a CPU 162, the memory 164 configured by a storage device, a communication interface (I/F) 166, and the like. Note that an image processing program is stored in the memory 164. The display/operation unit 170 is a graphical user interface for displaying images and for receiving various instructions. The display/operation unit 170 includes a display 172 and an input/instruction device 174 such as a touch panel.

The CPU 162 is an example of a "processor" of technology disclosed herein. The memory 164 is an example of a "computer-readable storage medium" of technology disclosed herein. The control unit 160 is an example of a "computer program product" of technology disclosed herein. The server 140 is an example of an "image processing device" of technology disclosed herein.

The configuration of the viewer 150 is similar to that of the server 140, and so description thereof is omitted.

Figure 5:
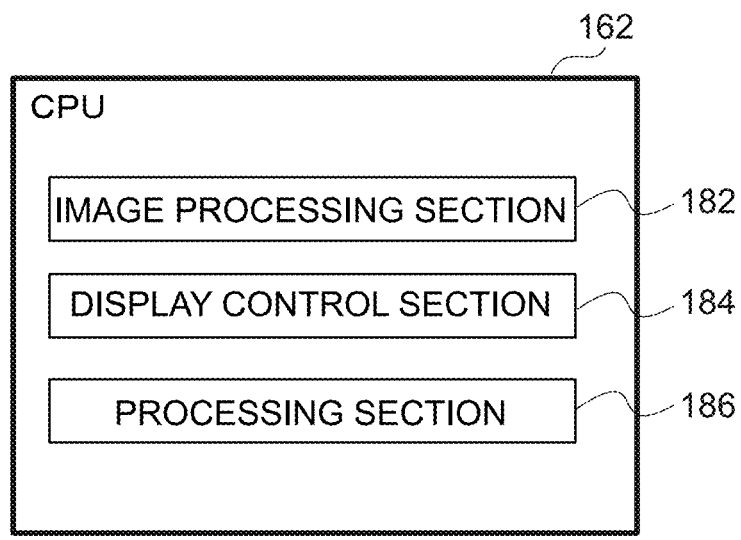
FIG. 5 is a functional block diagram of a CPU 162 of a server 140.

Next, description follows regarding each of various functions implemented by the CPU 162 of the server 140 executing the image processing program, with reference to FIG. 5. The image processing program includes an image processing function, a display control function, and a processing function. By the CPU 162 executing the image processing program including each of these functions, the CPU 162 functions as an image processing section 182, a display control section 184, and a processing section 186, as illustrated in FIG. 5.

The image processing section 182 is an example of a "detection section" of technology disclosed herein.

The image processing section 182 is an example of a "computation section", "projection section", and "generation section" of technology disclosed herein.

Figure 6:
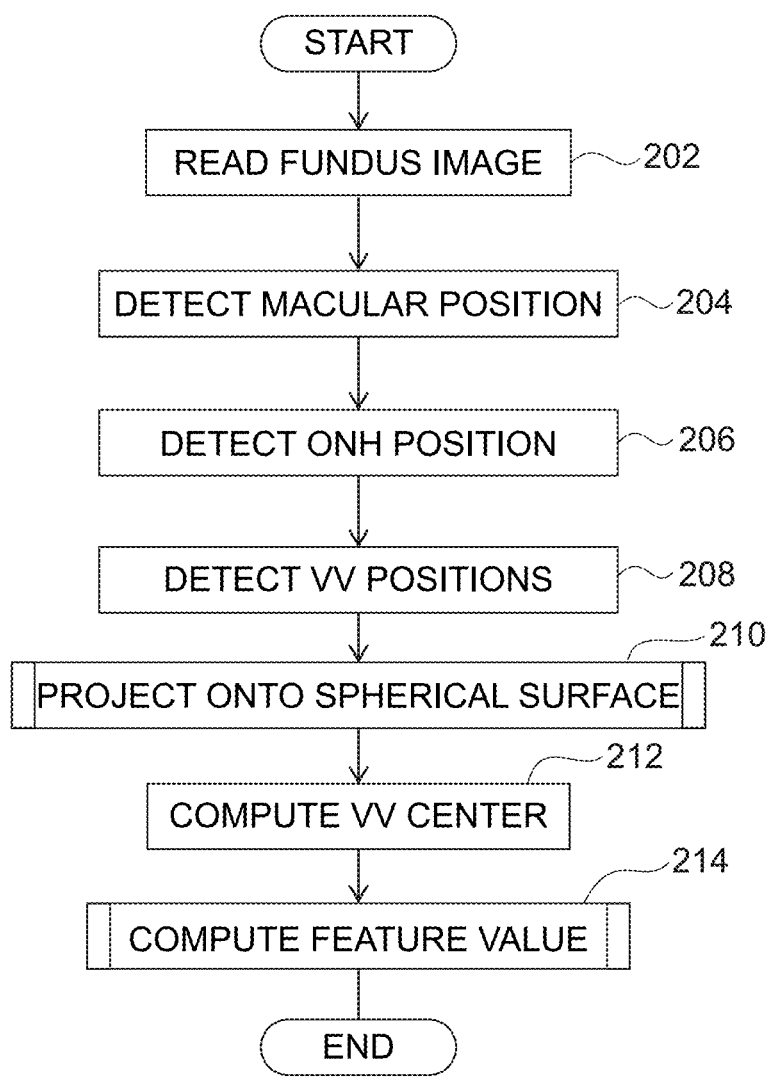
FIG. 6 is a flowchart of image processing executed by a server 140.

Next, with reference to FIG. 6, detailed description follows regarding image processing by the server 140. The image processing illustrated in the flowchart of FIG. 6 is implemented by the CPU 162 of the server 140 executing an image processing program.

Figure 10A:
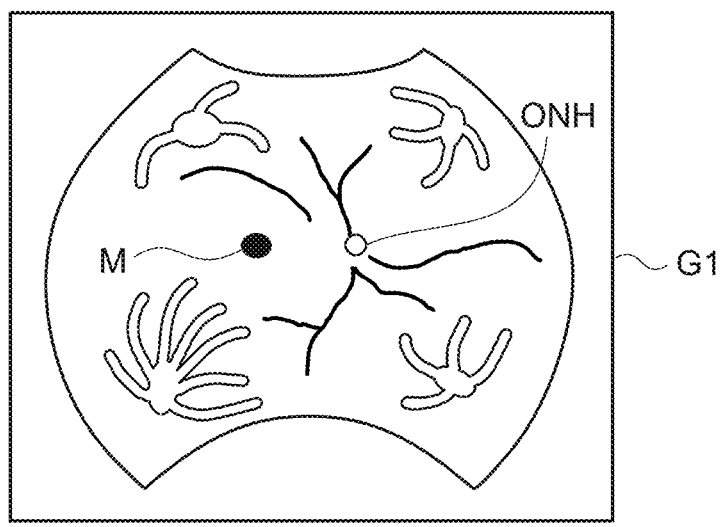
FIG. 10A is a diagram illustrating a color fundus image G1.

The image processing program is executed when the server 140 has received image data of fundus images (for example, a UWF fundus image) imaged by the ophthalmic device 110 and when a choroidal vascular image has been generated based on image data of a first fundus image (red fundus image) and a second fundus image (green fundus image) in the received fundus images. FIG. 10A illustrates a RGB color fundus image G1 in the received fundus images. Note that the ophthalmic device 110 transmits patient information (such as the patient name, patient ID, patient age, and visual acuity) to the server 140 together with the image data.

The choroidal vascular image is generated in the following manner.

Explanation first follows regarding information included in the first fundus image (red fundus image) and second fundus image (green fundus image).

The structure of the eye is configured by the vitreous body covered by plural layers that each have a different structure. These plural layers include the retina, the choroid, and the sclera in sequence from the side closest to the vitreous body outward. R light passes through the retina and travels as far as the choroid. Accordingly, the first fundus image (red fundus image) includes information relating to blood vessels (retinal blood vessels) present in the retina and information relating to blood vessels (choroidal blood vessels) present in the choroid. By contrast, G light only travels as far as the retina. Accordingly, the second fundus image (green fundus image) includes information relating to the blood vessels (retinal blood vessels) present in the retina. Thus a choroidal vascular image can be obtained by extracting the retinal blood vessels from the second fundus image (green fundus image) and removing the retinal blood vessels from the first fundus image (red fundus image).

Figure 10B:
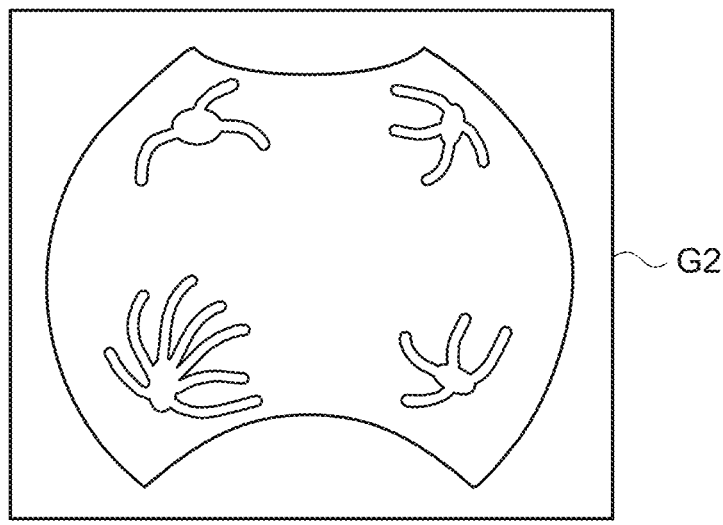
FIG. 10B is a diagram illustrating a choroidal vascular image G2.

Next, description follows regarding a method for generating a choroidal vascular image. The image processing section 182 of the server 140 subjects the second fundus image (green fundus image) to black hat filter processing so as to extract the retinal blood vessels from the second fundus image (green fundus image). Next, the image processing section 182 removes the retinal blood vessels from the first fundus image (red fundus image) by employing the retinal blood vessels extracted from the second fundus image (green fundus image) to perform in-painting processing. Namely, processing is performed that uses position information relating to the retinal blood vessels extracted from the second fundus image (green fundus image) to infill the retinal vascular structure in the first fundus image (red fundus image) with the same pixel values to those of surrounding pixels. The image processing section 182 then subjects the image data of the first fundus image (red fundus image) from which the retinal blood vessels have been removed to contrast-limited adaptive histogram equalization (CLAHE), thereby emphasizing the choroidal blood vessels in the first fundus image (red fundus image). A choroidal vascular image G2 as illustrated in FIG. 10B is obtained thereby. The generated choroidal vascular image is stored in the memory 164 associated with the patient information.

Moreover, although the choroidal vascular image is generated from the first fundus image (red fundus image) and the second fundus image (green fundus image), the image processing section 182 may next generate a choroidal vascular image employing the first fundus image (red fundus image) or the IR fundus image imaged with IR light. Regarding the method used to generate the choroidal fundus image, the disclosures of Japanese Patent Application No. 2018-052246 filed on Mar. 20, 2018 and WO No. 2019/181981A1 are incorporated in their entireties by reference herein.

At the start of the image processing program, at step 202 of FIG. 6, the processing section 186 reads from the memory 164 the choroidal vascular image G2 (see FIG. 10B) and the green fundus image, as fundus images.

At step 204, the image processing section 182 estimates the macula position from the green fundus image. Specifically, the macula is a dark region in the green fundus image, and so the image processing section 182 detects a region of a specific number of pixels having the lowest pixel values in the green fundus image read as described above as the position of the macula. The coordinates indicating the position of the macula are stored in the memory 164 associated with the patient information.

At step 206 the image processing section 182 detects a position of the optic nerve head ONH from the green fundus image. Specifically, the image processing section 182 detects the position of the optic nerve head ONH in the green fundus image by pattern matching a predetermined optic nerve head image against the green fundus image that was read. The coordinates indicating the position of the optic nerve head ONH are stored in the memory 164 associated with the patient information.

However, the optic nerve head is a brightest region in the green fundus image, and so a region of a specific number of pixels with the greatest pixel value in the green fundus image that was read may be detected as the position of the optic nerve head.

The choroidal vascular image is produced by processing the red fundus image and the green fundus image in the manner described above. Thus when the coordinate system of the green fundus image is overlaid on the coordinate system of the choroidal vascular image, the respective positions in the coordinate system of the green fundus image are the same as the respective positions in the coordinate system of the choroidal vascular image. The respective positions on the choroidal vascular image corresponding to the respective positions of the macula and the optic nerve head detected in the green fundus image are therefore the respective positions of the macula and the optic nerve head.

Thus in the processing of step 204, the position of the macula may be detected from the choroidal vascular image instead of from the green fundus image. Similarly, in the processing of step 206, the position of the optic nerve head may be detected from the choroidal fundus image instead of from the green fundus image.

At step 208 the image processing section 182 detects vortex vein (hereafter referred to as VV) positions in the choroidal vascular image. The vortex veins VV are flow paths of blood flow flowing into the choroid, and there are plural vortex veins present toward the posterior pole from an equatorial portion of the eyeball.

The image processing section 182 finds the blood vessel running direction at each of the pixels in the choroidal vascular image. Specifically, the image processing section 182 repeatedly performs the following processing on all the pixels. Namely, the image processing section 182 sets a region (cell) configured by plural pixels surrounding a given pixel at the center. Next, the image processing section 182 calculates a brightness gradient direction for each pixel of the cell (for example, expressed as an angle from 0° to just under 180°. Note that calculation is based on the brightness values of the pixels surrounding the pixel, with 0° defined as a direction of a straight line (namely a horizontal line)). The gradient direction calculation is performed for all of the pixels in the cell.

Next, in order to create a histogram with nine bins (such as bin widths of 20°) of gradient direction centered on 0°, 20°, 40°, 60°, 80°, 100°, 120°, 140°, and 160°, the number of pixels inside the cell that have a gradient direction corresponding to each of the bins is counted. The width of a single bin in the histogram is 20°, and the 0° bin is set with the number (i.e. count value) of pixels in the cell having a gradient direction of from 0° up to but not including 10° or having a gradient direction of from 170° up to but not including 180°. The 20° bin is set with the number (i.e. count value) of pixels in the cell having a gradient direction of from 10° up to but not including 30°. The count values for the bins 40°, 60°, 80°, 100°, 120°, 140°, and 160° are set in a similar manner. Due to there being nine bins in the histogram, the blood vessel running direction at each of the pixels is defined as being in one of nine direction types. Note that the resolution of the blood vessel running direction can be raised by narrowing the width of each bin and increasing the number of bins. The count values of each of the bins (i.e. the vertical axis in the histogram) is normalized, and a histogram is created for each analysis point.

Next, the image processing section 182 identifies the blood vessel running direction at each analysis point from the histogram. Specifically, the bin with the angle having the smallest count value (such as) 60° is identified, and 60°, which is the gradient direction of the identified bin, is identified as the blood vessel running direction of the pixel. The gradient direction having the smallest count is taken as the blood vessel running direction for the following reason. There is a small brightness gradient in the blood vessel running direction, however, there is a larger brightness gradient in other directions (for example, there is a large difference in brightness between blood vessels and tissue other than blood vessels). Thus when the respective histograms of brightness gradient have been created for each of the pixels, then the count value becomes small in the bin for the blood vessel running direction. Histograms are similarly created for each of the pixels in the choroidal vascular image, and the blood vessel running direction is computed at each of the pixels. The computed blood vessel running directions at each of the pixels are stored in the memory 164 associated with the patient information.

The image processing section 182 then sets initial positions of imaginary particles at M individual positions at uniform spacings in the choroidal vascular image vertically and at N individual positions therein horizontally, namely a total of L individual positions. For example, if M=10 and N=50, then a total of L=500 individual initial positions are set.

Figure 10C:
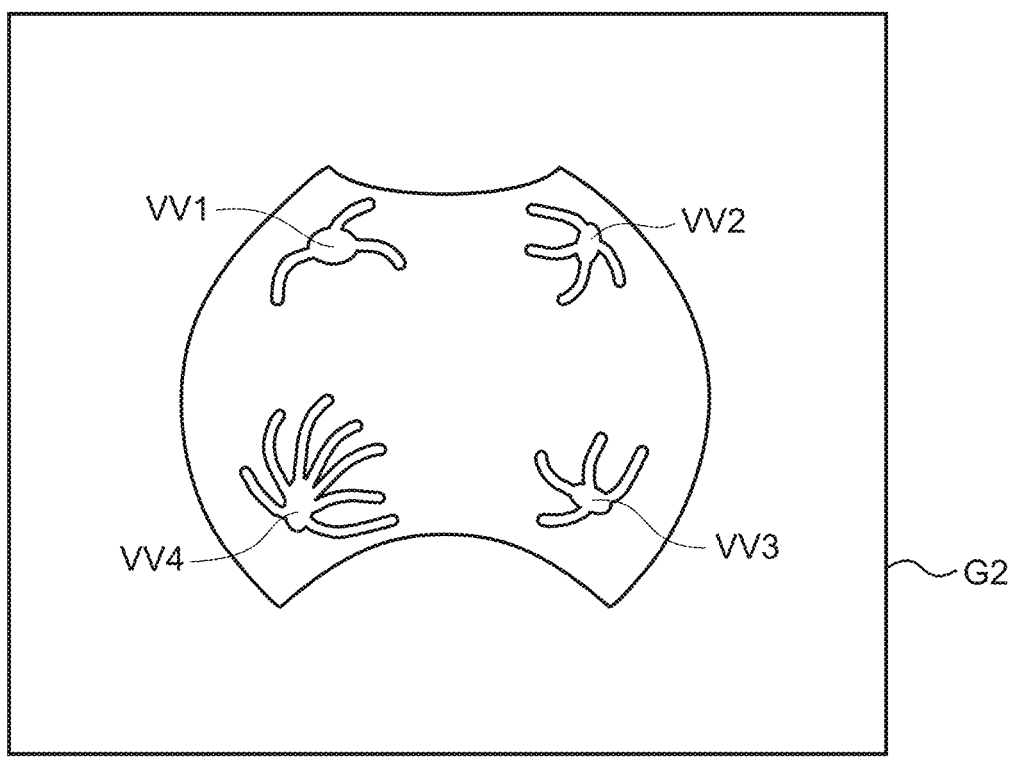
FIG. 10C is a diagram illustrating a pattern of four detected vortex veins VV1 to VV4.

Furthermore, the image processing section 182 acquires the blood vessel running direction at a first position (one of the L individual positions), moves the imaginary particle by a specific distance along the acquired blood vessel running direction, repeats acquisition of the blood vessel running direction but this time at the position moved to, and then moves the imaginary particle by the specific distance along this acquired blood vessel running direction. Such movements of a specific movement distance along the acquired blood vessel running direction are repeated a preset number of times. The above processing is executed for all of the L individual positions. At the point in time when all of the L individual imaginary particles have been moved the preset number of times, a point where a given number of imaginary particles or more have collected together is detected as a VV position. FIG. 10C illustrates a pattern of four detected vortex veins VV1 to VV4.

The numbers of the detected VVs and VV position information (for example coordinates indicating the VV positions on the choroidal vascular image) are stored in the memory 164 associated with the patient information. Detection of the vortex veins VV may be performed not only with the choroidal vascular image, but also using various fundus images. These include color fundus images imaged with various wavelengths of visible light, such as the red fundus image and the green fundus image, fluoroscopic fundus images using fluoroscopy, two-dimensional images (en-face OCT images) generated from three-dimensional OCT volume data, and also binarized images obtained by performing image processing on such images, and vascular images in which the blood vessels have been subjected to emphasis processing. Furthermore, a choroidal vascular image generated by processing to extract choroidal blood vessels from a vascular image may also be employed.

At step 210 the image processing section 182 projects the optic nerve head ONH, the macula M, and each of the VVs onto a spherical surface of an eyeball model.

Figure 7:
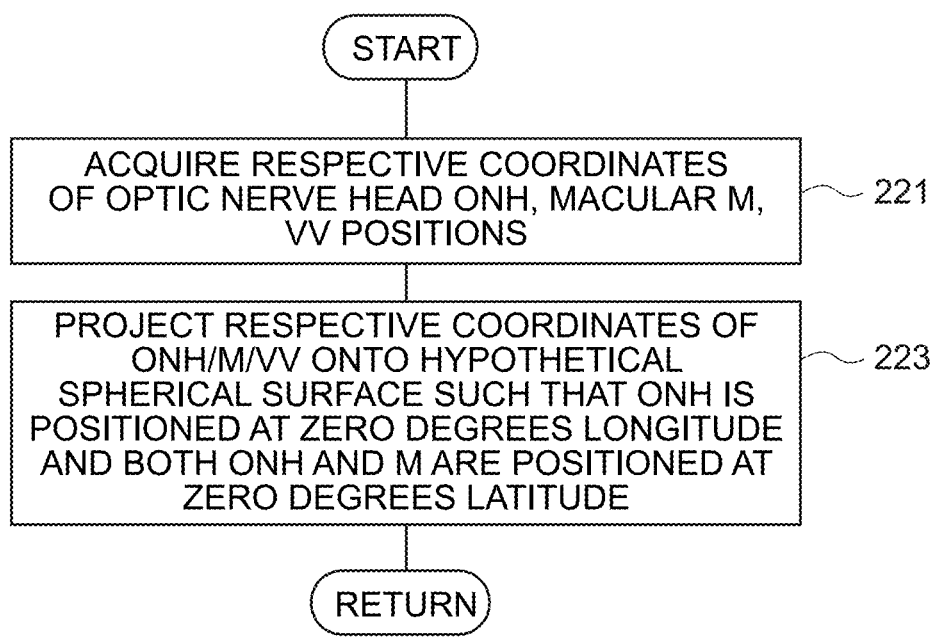
FIG. 7 is a flowchart illustrating projection processing of step 210 of FIG. 6.

FIG. 7 illustrates a flowchart of the projection processing of step 210 of FIG. 6. At step 221 of FIG. 7, the processing section 186 acquires, from the memory 164, respective coordinates (X, Y) on the fundus image (UWF fundus image) of the optic nerve head ONH, the macula M and of the VV positions in the choroidal fundus image corresponding to the patient information.

Figure 11:
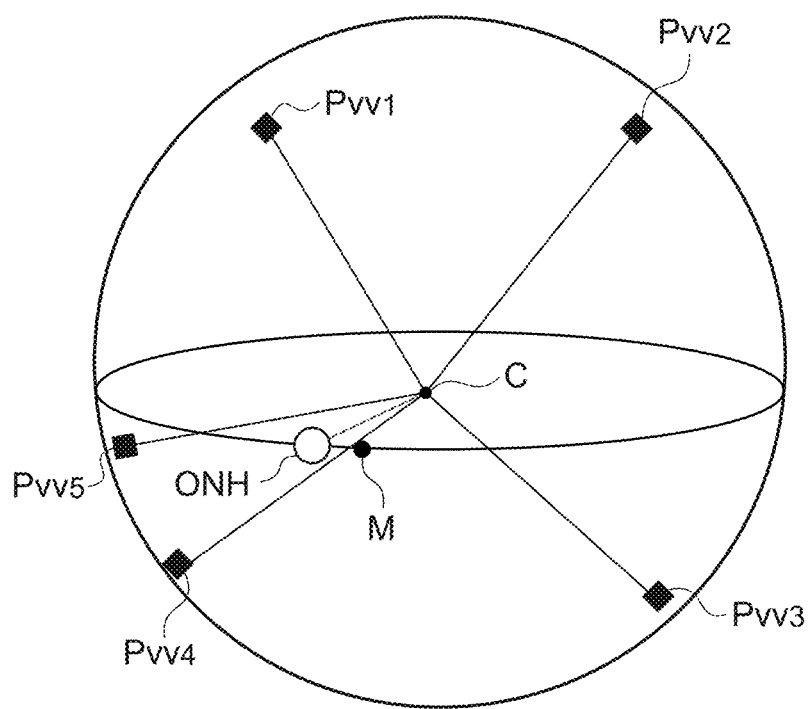
FIG. 11 is a diagram illustrating an eyeball model in which an optic nerve head ONH is at zero degrees longitude, and the optic nerve head ONH, macula M, and five VV positions Pvv1 to Pvv5 are projected onto a hypothetical spherical surface (hypothetical eyeball surface).

At step 223 the image processing section 182 performs processing to project the respective coordinates of the optic nerve head ONH, the macula M, and the VV positions onto a hypothetical spherical surface (eyeball surface or eyeball model surface) corresponding to the fundus of an eyeball model illustrated in FIG. 11. The eyeball model is a spherical body model having C as the center of the eyeball and a radius of R (eye axial length of 2R). A spherical surface of this eyeball model is defined as the eyeball surface. Points on the eyeball surface are identified by positions in latitude and longitude.

The optic nerve head ONH is projected so as to be a datum point (longitude 0°, latitude) 0°, and so that the macula M has a latitude of 0°. The VV positions are also projected onto the eyeball surface as Pvv1, Pvv2, Pvv3, Pvv4, Pvv5 (for a case in which there are five vortex veins VVs detected in the examined eye) with the optic nerve head ONH as the datum point.

Thus the optic nerve head ONH and the macula M are respectively projected onto a 0° line of latitude, and a line segment connecting the optic nerve head ONH and the macula M on the eyeball surface is positioned on the 0° latitude line.

The eyeball model is also defined in three-dimensional space (X, Y, Z), and is defined in image processing memory space. As described above, the X direction is a horizontal direction for a case in which the ophthalmic device 110 has been placed on a horizontal surface, and the X direction is a left-right direction of the examined eye since the patient is positioned at a position facing toward the ophthalmic device 110. The Y direction is a direction perpendicular to the horizontal surface, and is the up/down direction of the examined eye. The Z direction is a direction connecting the center of a pupil of an anterior eye portion of the examined eye 12 to a center of the eyeball.

A transformation equation is stored in the memory 164 for performing a reverse stereographic projection transformation of the respective coordinates (X, Y) of positions on a two-dimensional fundus image (UWF fundus image) into three-dimensional space (X, Y, Z). This transformation equation in the present exemplary embodiment transforms (i.e. projects) such that the position of the optic nerve head ONH becomes a datum point on the eyeball surface (a position where both longitude and latitude are) 0° and such that the position of the macula M becomes a position at 0° latitude. Furthermore, using this transformation equation the positions (X, Yl) of each of the VVs on a two-dimensional fundus image are transformed (i.e. projected) into the positions Pvv1 to Pvv5 on a three-dimensional eyeball surface.

The coordinates (X, Y, Z) of the positions Pvv1 to Pvv5 of the vortex veins VV1 to VV5 on the eyeball surface are stored, together with the three-dimensional coordinates of the optic nerve head ONH and the macula M, in the memory 164 associated with identification information of the patient.

After the processing of step 223 of FIG. 7 has been completed, the image processing proceeds to step 212 of FIG. 6.

At step 212 the image processing section 182 computes a point at the center of distribution of the plural vortex veins (hereafter referred to as the VV center). The VV center is the center point of the distribution of the respective positions of the plural VVs. The center of distribution point can be found by first finding vectors from the center point C of the eyeball model to the vortex vein positions (Pvv1 and the like), and then finding a composite vector that combines the plural respective vectors to the VVs.

Figure 8:
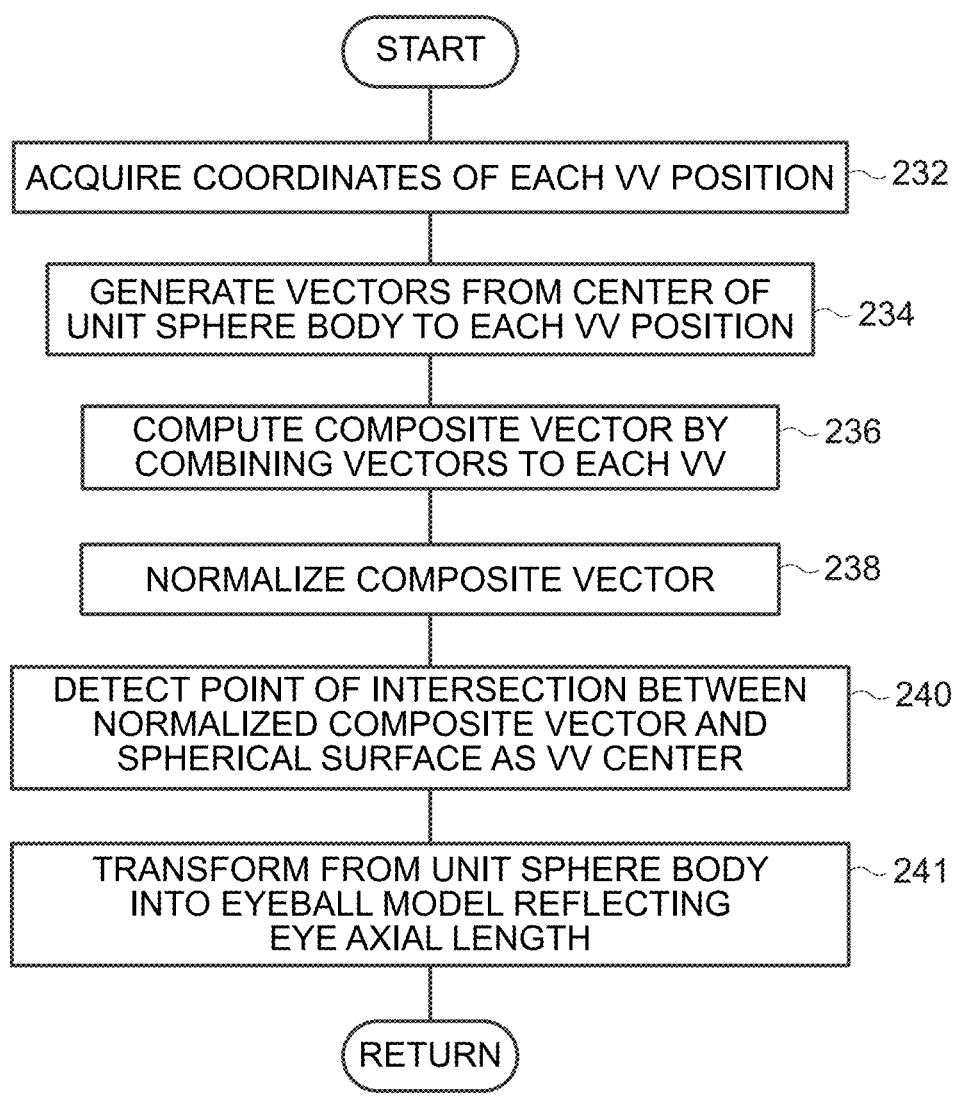
FIG. 8 is a flowchart illustrating VV center computation processing of step 212 of FIG. 6.

FIG. 8 illustrates a flowchart of processing to compute the VV center of step 212 of FIG. 6. Explanation follows regarding a case of FIG. 8 in which five vortex veins VV have been detected in the examined eye.

At step 232 of FIG. 8 the processing section 186 acquires from the memory 164 the coordinates (x1, y1, z1) to (x5, y5, z5) of the respective VV positions Pvv1 to Pvv5 associated with the patient information. The eyeball model employed here is a unit sphere having a radius of unit length 1.

Figure 12A:
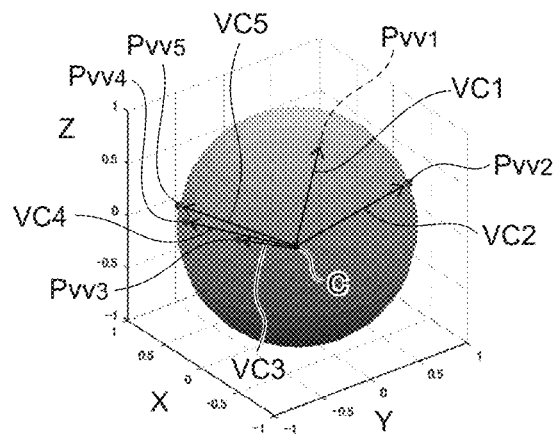
FIG. 12A is a diagram illustrating vectors VC1 to VC5 from a center C of a spherical body to respective VV positions Pvv1 to Pvv5, with the eyeball model viewed obliquely.
Figure 12B:
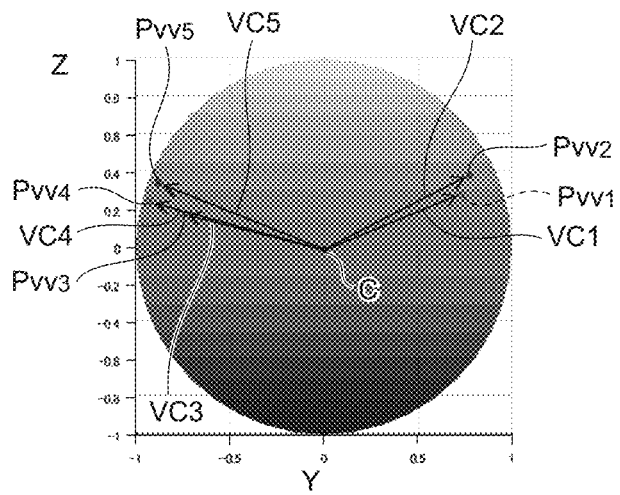
FIG. 12B is a diagram illustrating vectors VC1 to VC5 from a center C of a spherical body to respective VV positions Pvv1 to Pvv5, with the eyeball model viewed from the side.
Figure 12C:
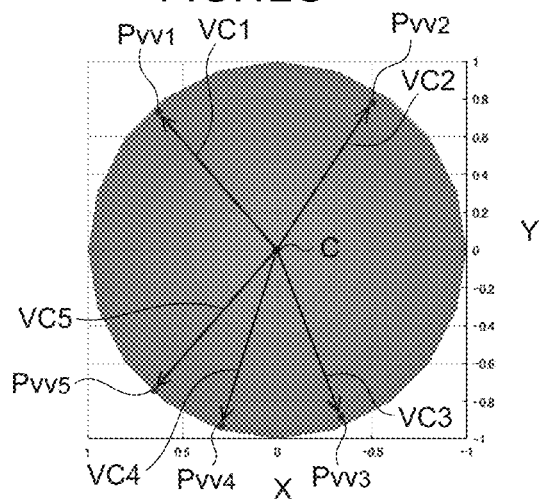
FIG. 12C is a diagram illustrating vectors VC1 to VC5 from a center C of a spherical body to respective VV positions Pvv1 to Pvv5, with the eyeball model viewed from above.

At step 234 the image processing section 182 generates vectors VC1 to VC5 from the enter C of the eyeball model spherical body to the respective VV positions Pvv1 to Pvv5, as illustrated in FIG. 12A to FIG. 12C, as Equations (1).

$$\vec{VV1}=(x1, y1, z1)$$
$$\vec{VV2}=(x2, y2, z2)$$
$$\vec{VV3}=(x3, y3, z3)$$
$$\vec{VV4}=(x4, y4, z4)$$
$$\vec{VV5}=(x5, y5, z5) \quad \text{Equations (1)}$$

The length of each of the vectors VC is the unit length 1. FIG. 12A to FIG. 12C are diagrams looking at the unit sphere obliquely, from the side, and from above.

Figure 13A:
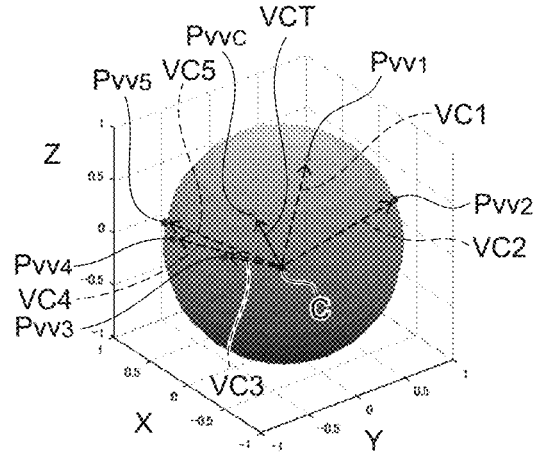
FIG. 13A is a diagram illustrating a composite vector VCT computed by combining vectors VC1 to VC5 to respective VVs, with the eyeball model viewed obliquely.
Figure 13B:
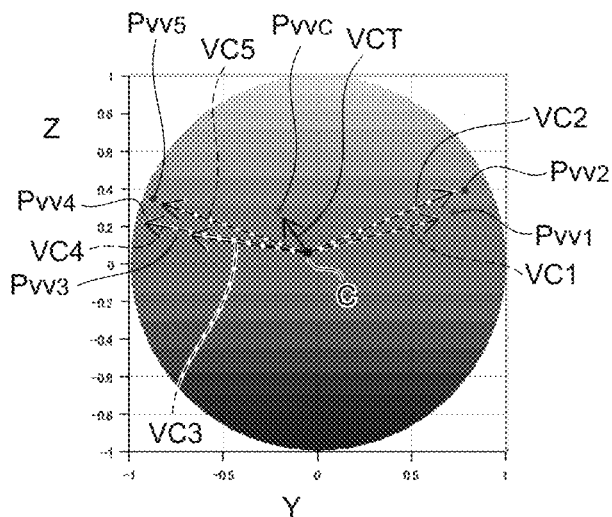
FIG. 13B is a diagram illustrating a composite vector VCT computed by combining vectors VC1 to VC5 to respective VVs, with the eyeball model viewed from the side.
Figure 13C:
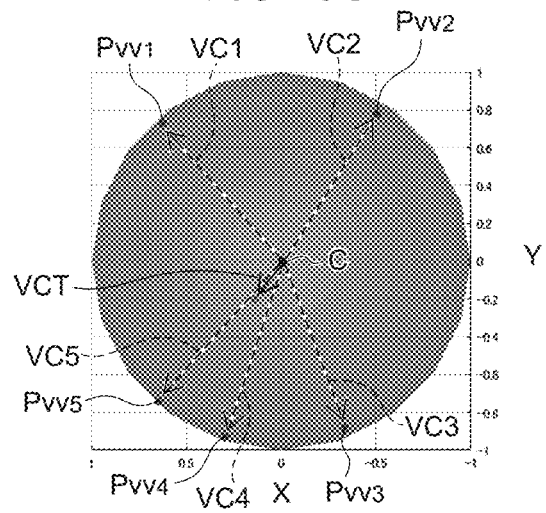
FIG. 13C is a diagram illustrating a composite vector VCT computed by combining vectors VC1 to VC5 to respective VVs, with the eyeball model viewed from above.

At step 236 the image processing section 182 computes the composite vector VCT (see VV composition of Equation (2)) by combining the vectors VC1 to VC5 to the respective VVs, as illustrated in FIG. 13A to FIG. 13C. Specifically, this is processing to take the sum of the coordinate values of the respective vectors VC as represented by Equation (2).

$$\vec{VV}\text{composition}=(x1+ \ldots x5, y1+ \ldots y5, z1+ \ldots z5) \quad \text{Equation (2)}$$

The coordinates of the point Pvvc defined by the composite vector VCT from the center C is defined as the sum of the coordinates X, Y, Z of each of the positions Pvv1 to Pvv5. The point Pvvc is a center of distribution of the positions VV1 to VV5 in three-dimensional space. The point Pvvc is a position minimizing the total distance (e.g. a Euclidean distance) between the respective positions VV1 to VV5. The point Pvvc is a generally a position at the inside of the spherical body of the eyeball model. FIG. 13A to FIG. 13C are diagrams looking at the unit sphere eyeball model obliquely, from the side, and from above.

Figure 14A:
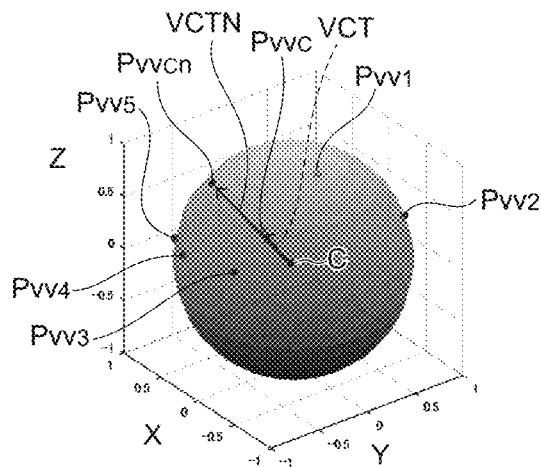
FIG. 14A is a diagram illustrating a normalized composite vector VCTN obtained by normalizing a length of a composite vector VCT so as to be a length of a vector VC1 (1, for example), with the eyeball model viewed obliquely.
Figure 14B:
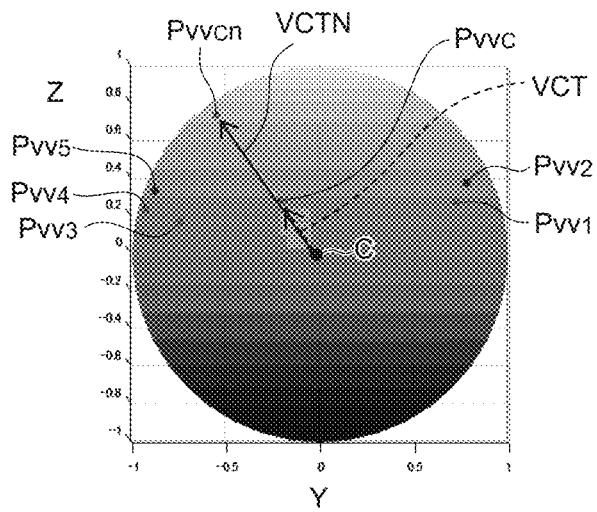
FIG. 14B is a diagram illustrating a normalized composite vector VCTN obtained by normalizing a length of a composite vector VCT so as to be a length of a vector VC1 (1, for example), with the eyeball model viewed from the side.
Figure 14C:
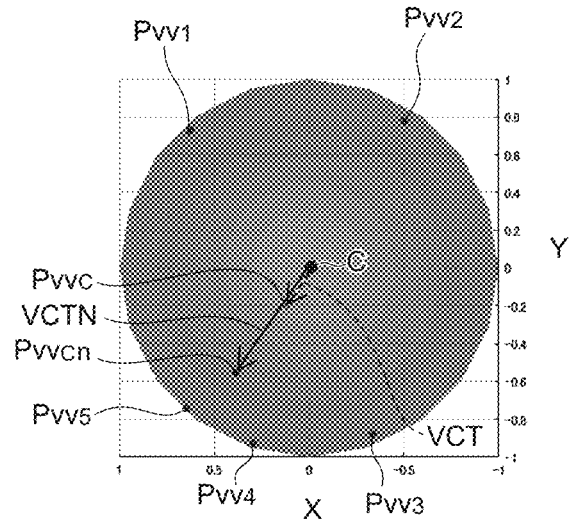
FIG. 14C is a diagram illustrating a normalized composite vector VCTN obtained by normalizing a length of a composite vector VCT so as to be a length of a vector VC1 (1, for example), with the eyeball model viewed from above.

At step 238 the image processing section 182 normalizes the composite vector VCT such that the length of the composite vector is a unit length 1, as illustrated in FIG. 14A to FIG. 14C. A composite vector VCTN normalized in this manner (see VV center of Equation (3)) is obtained as Equation (3).

$$\vec{VV}\text{center} = \frac{VV\text{composition}}{|VV\text{composition}|} \quad \text{Equation (3)}$$

A point Pvvcn defined at step 240 by the normalized composite vector VCTN from the center C is a position on an eyeball surface of the unit sphere eyeball model. The point Pvvcn is a point of intersection between the normalized composite vector VCTN and the unit sphere eyeball surface. The point Pvvcn is a center of distribution of the plural respective VV positions on the eyeball model spherical surface.

This position may also be defined as a position minimizing a total distance (e.g. a great circle distance on the eyeball model spherical surface) between the plural respective VV positions and the center of distribution. FIG. 14A to FIG. 14C are diagrams looking at the unit sphere eyeball model obliquely, from the side, and from above.

The center of distribution position of the plural vortex veins on the unit sphere spherical surface is found at step 240. The latitude and longitude of the center of distribution vortex veins is accordingly found.

At step 241 the image processing section 182 enlarges the unit sphere to an eyeball model of eye axial length 2R. Namely, if the eye axial length of the examined eye is 24 mm (namely, 2×12 mm, R=12) then a transformation is performed to a sphere of radius 12 mm.

Additionally at step 241, the image processing section 182 extracts respective coordinates on the eyeball surface for the optic nerve head ONH, the macula M, the vortex veins VV1 to VV5, and the center of vortex vein distribution Pvvcn in the eyeball model reflecting the eye axial length of the examined eye, or extracts the latitude and longitude for the macula M, the vortex veins, and the center of vortex vein distribution computed with reference to the optic nerve head. Information of the extracted coordinates or latitude and longitude is stored in the memory 164 associated with the patient information. Both the coordinates and the latitude and longitude may be saved in the memory 164.

When the processing of step 241 of FIG. 8 is completed, the image processing proceeds to step 214 of FIG. 6.

At step 214, the image processing section 182 computes at least one feature value indicating a positional relationship between the position of an identified site on the eyeball model and plural target positions including the VV center. Examples of the identified site include the optic nerve head, the macula, the pupil center (namely, the apex of the cornea), and the fovea. Explanation follows regarding a case in which the optic nerve head serves as the identified site.

Figure 9:
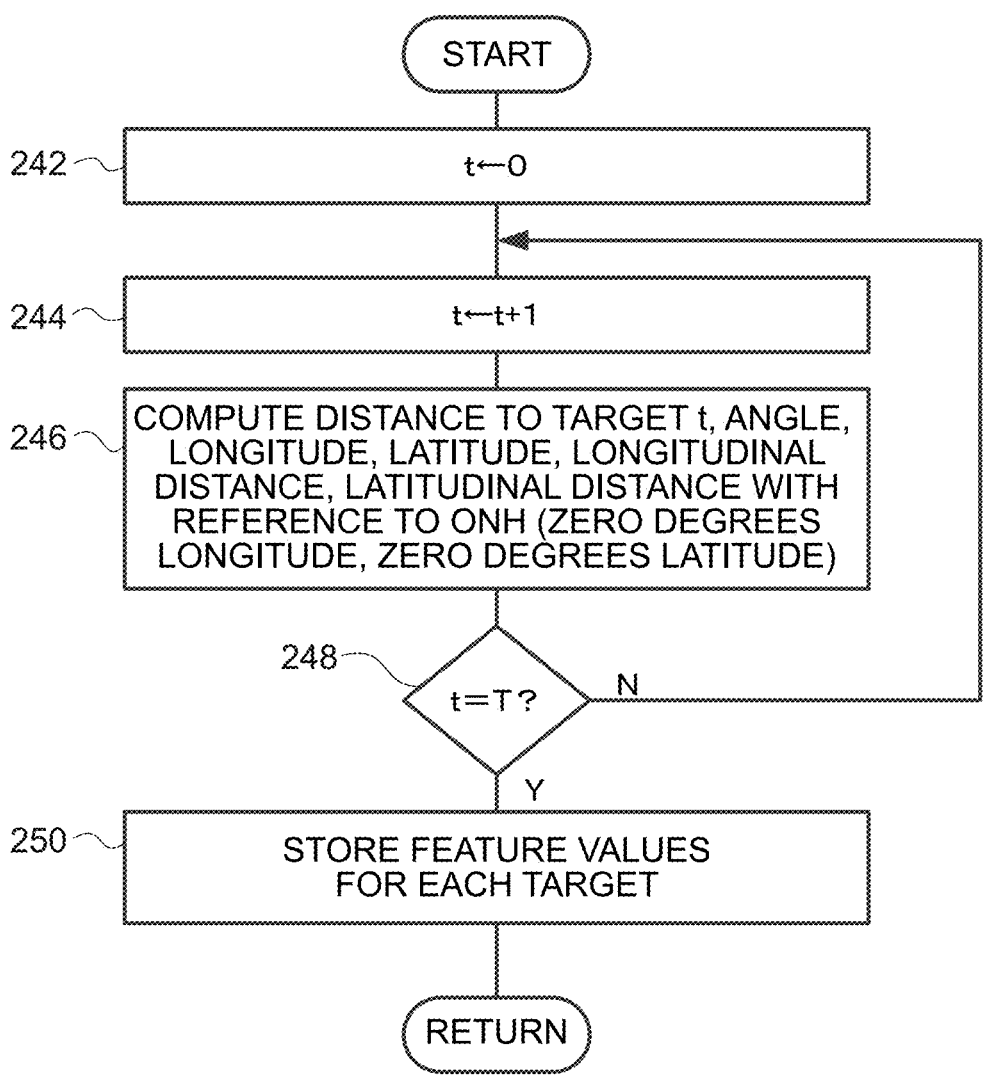
FIG. 9 is a flowchart of feature value computation processing of step 214 of FIG. 6.

FIG. 9 is a detailed flowchart of feature value computation processing of step 214 of FIG. 6. At step 242 of FIG. 9, the image processing section 182 sets a variable t, to identify feature value computation targets, to zero and at step 244 the image processing section 182 increments the variable t by one. For example, the VV center, VV1, VV2, and so on are identified by variable t=1, 2, 3, and so on.

At step 246 the image processing section 182 computes a great circle distance and angle to the target t, and the latitude and longitude of the position of the target t, using the optic nerve head ONH as the datum point (for example longitude: 0°, latitude:)0°, and then computes a feature value of the target t as the longitude distance and latitude distance from the datum point to the target t. This is more specifically performed in the following manner.

First explanation follows regarding a case in which the feature value is computed with the variable t=1, namely the VV center, as the target.

Figure 15:
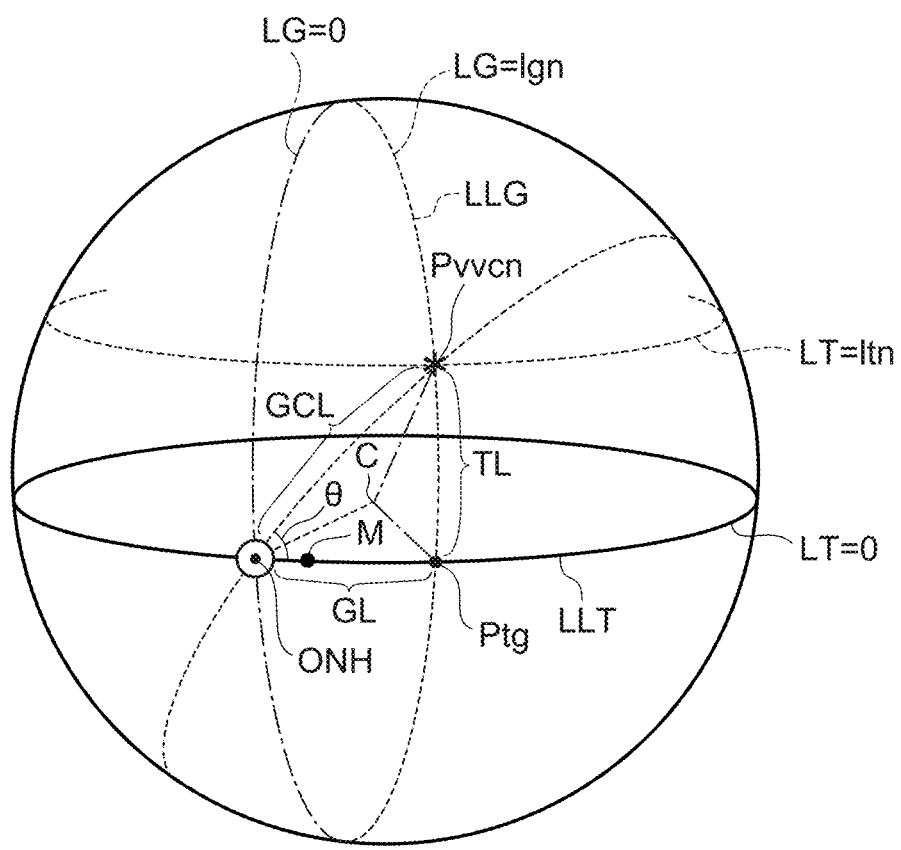
FIG. 15 is an explanatory diagram of a concept of feature values indicating positional relationships between an optic nerve head ONH and VV center.

As illustrated in FIG. 15, the image processing section 182 computes a great circle distance GCL between the optic nerve head ONH and the VV center (point Pvvcn) using spherical trigonometry. A great circle is defined as the cut section when a spherical body is cut so as to pass through the center C of the eyeball model spherical body, and the great circle distance is the distance on a great circle arc connecting the two points subject to distance measurement on the spherical surface (the optic nerve head ONH and the VV center (point Pvvcn)).

The image processing section 182 then, as illustrated in FIG. 15, computes an angle 0 formed between a first line segment GCL connecting the macula M position and the optic nerve head ONH position on a great circle, and a second line segment GCL connecting the optic nerve head ONH position and the VV center Pvvcn position, by computation using conformal projection or spherical trigonometry.

The method of calculating the distance and angle described above is similar to methods described in International Publication PCT/JP2019/016653 filed Apr. 18, 2019. The methods of calculating the distance and angle described in International Publication PCT/JP2019/016653 filed Apr. 18, 2019 (WO No. 2019 203310 (disclosed internationally on Oct. 24, 2019) are incorporated by reference in their entirety to the present specification.

The image processing section 182 then computes the longitude (LG=lgn) and latitude (LT=ltn) of the VV center Pvvon as illustrated in FIG. 15. As described above, the eyeball model is defined in three-dimensional space such that a position where the latitude and longitude is 0° is at the position of the optic nerve head ONH serving as the datum point, and the position of the macula M is arranged so as to be positioned on the 0° latitude line LLT.

The image processing section 182 computes the longitude (LG=lgn) and latitude (LT=ltn) of the VV center Pvvon by transforming the coordinates (x, y, z) of the VV center Pvvcn in three-dimensional space according to a specific transformation equation such as the one below in which the position of the optic nerve head ONH (X, Y, Z)=(1, 0, 0).

longitude $LG = \arctan(y/x)$ latitude $LT = \arctan(z/\sqrt{(x^2+y^2)})$

The (LG (longitude), latitude (LT)) of the VV center Pvvon are thereby computed as (lgn, ltn).

As illustrated in FIG. 15, the image processing section 182 computes the latitudinal distance TL and the longitudinal distance GL of the VV center Pvvcn using spherical trigonometry.

A latitudinal distance TL of the VV center Pvvcn is a great circle distance between the VV center Pvvcn along the line of longitude LLG passing through the VV center Pvvcn and an intersection point Ptg between this line of longitude LLG and the line of latitude LLT latitude 0.

A longitudinal distance GL of the VV center Pvvon is a great circle distance between the position of the optic nerve head ONH along the line of latitude LLT of latitude 0 and the intersection point Ptg.

The feature value computation processing proceeds to step 248 when the feature values described above have been computed for each of targets identified by the variable t as described above.

At step 248 the image processing section 182 determines whether or not the variable t is equivalent to a total number T of the targets for feature value computation.

There are still targets for which feature values have not been computed in cases in which the variable t is not equivalent to the total number T, and so the feature value computation processing returns to step 244 and the above processing (namely, steps 244 to 248) is executed.

In cases in which the variable t=2 onwards, the image processing section 182 computes the above distances, angles, latitude, longitude, longitudinal distance, and latitudinal distance for targets of positions VV1 onwards, instead of for the VV center Pvvcn.

The feature values have been computed for all of the targets for which feature values are to be computed in cases in which the variable t is equivalent to the total number T, and so at step 250 the processing section 186 stores the respective feature values for each of the targets in a feature value table of the memory 164 associated with the patient information, as illustrated in FIG. 16. In the example illustrated in FIG. 16 the feature value table is provided with items including a patient ID, identification information of left or right eye, and eye axial length corresponding to the left or right eye. A feature value storage area is provided for each examined eye (left eye or right eye). The feature value storage area is stored with type information indicating the type of the target (optic nerve head, macula, vortex veins VV1 to VV5, VV center, etc.), and with feature value information for the distance, angle, latitude, longitude, longitudinal distance, and latitudinal distance. Note that coordinates on the eyeball surface of the optic nerve head ONH, the macula M, the vortex veins VV1 to VV5, and the VV center may be included in the feature value table.

Moreover, although explanation of the example described above is of a case in which the number of vortex veins is five, obviously the example described above is applicable to N vortex veins detected in the examined eye (wherein N is a natural number).

Furthermore, a displacement between the found optic nerve head position and the VV center position, and specifically a distance (great circle distance or the like) between the optic nerve head position and the VV center position, and a feature value defined by a direction from the optic nerve head to the VV center position (namely, a vector connecting the optic nerve head position and the VV center position together) may be found as some of the feature values. Moreover, a displacement between the macula position and the VV center position, and the displacement between a position of pathological change on the fundus and the VV center position, may similarly be found as feature values. These displacements may be taken as general numerical indicators of pathology.

The processing of step 214 of FIG. 6 is completed when the processing of step 250 has been completed, and so the image processing is ended.

Explanation next follows regarding a process to display the center of distribution and the like on the viewer 150 after the computation processing using the server 140 of the center of distribution of plural vortex veins.

Icons and buttons for instructing the generation of later described images (FIG. 17, FIG. 18) are displayed on a display screen of a display of the viewer 150. The user who is an ophthalmologist clicks a specific icon or the like during examination of the patient when they want to know the position of the VV center, and an instruction signal corresponding to the clicked icon or the like is transmitted from the viewer 150 to the server 140.

The server 140 receiving the instruction signal from the viewer 150 generates an image (FIG. 17, FIG. 18) corresponding to the instruction signal, and image data of the generated image is transmitted to the viewer 150 over the network 130. The viewer 150 receiving the image data from the server 140 displays an image on the display based on the received image data. The display screen generation processing of the server 140 is performed by a display screen generation program being actuated in the CPU 162 (the display control section 184).

Figure 17:
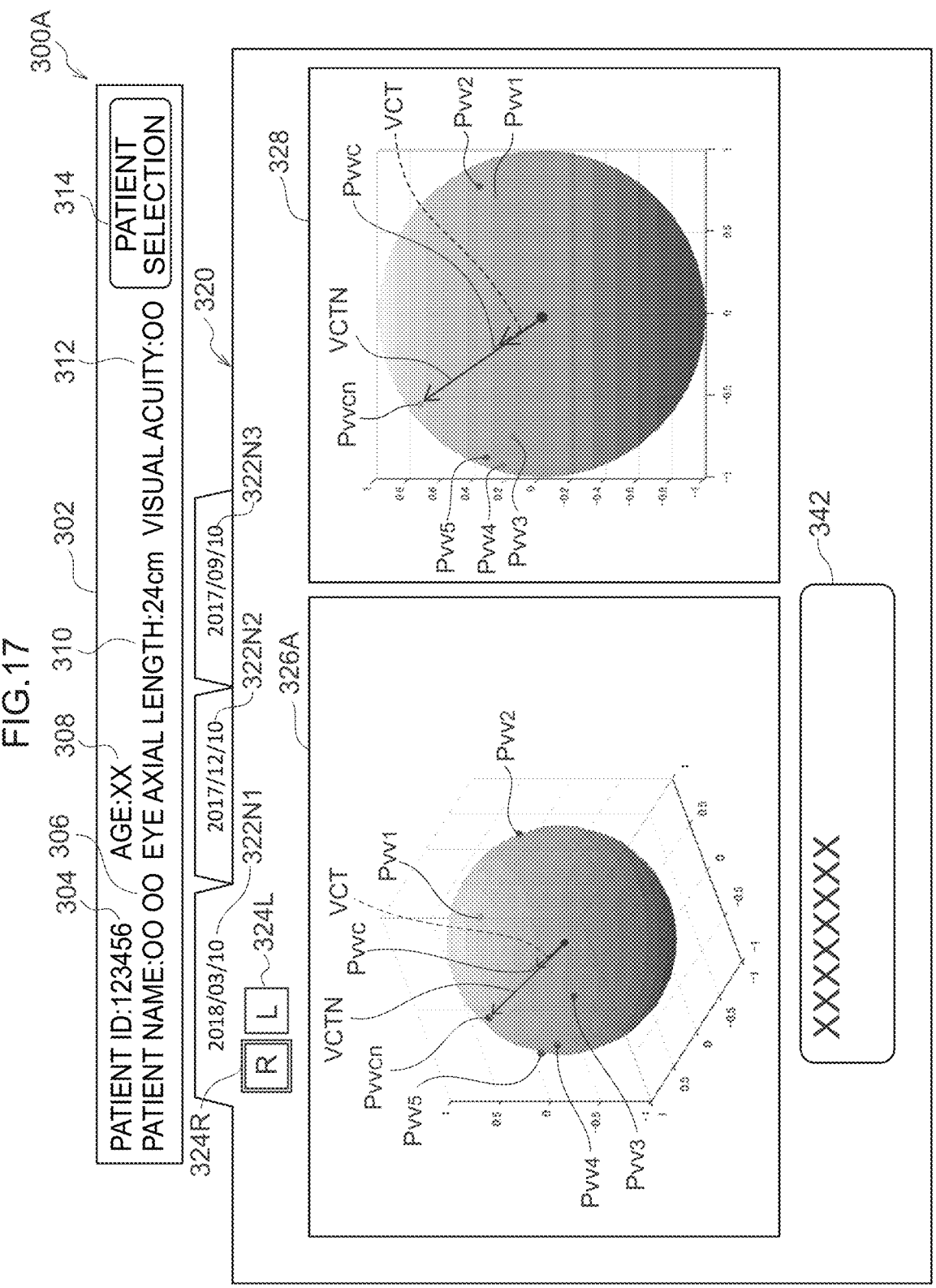
FIG. 17 is a diagram illustrating a first display screen 300A for displaying targets and feature values.

A first display screen 300A is displayed in FIG. 17 to display the targets and feature values. As illustrated in FIG. 17, the first display screen 300A includes a personal information display area 302 to display personal information about the patient, and an image display area 320.

The personal information display field 302 includes a patient ID display field 304, a patient name display field 306, an age display field 308, an eye axial length display field 310, a visual acuity display field 312, and a patient selection icon 314. Various information is displayed in the patient ID display field 304, the patient name display field 306, the age display field 308, the eye axial length display field 310, and the visual acuity display field 312. Note that a list of patients is displayed on the display 172 of the viewer 150 when the patient selection icon 314 is clicked, so as to let a user (ophthalmologist or the like) select the patient to be analyzed.

The image display area 320 includes an imaging date display field 322N1, a right eye information display field 324R, a left eye information display field 324L, a first eyeball model image display field 326A for the eyeball model viewed obliquely, a second eyeball model image display field 328 for the eyeball model viewed from the side, and an information display field 342. Comments and text are displayed in the information display field 342 during examination by the user (ophthalmologist or the like).

The example illustrated in FIG. 17 is able to display an eyeball model image for a case in which the fundus of the right eye (324R is illuminated) of a patient identified by the patient ID: 123456 was imaged on imaging days Mar. 10, 2018, Dec. 10, 2017, and Sep. 10, 2017. Note that the imaging date display field 322N1 and the right eye information display field 324R have been clicked, and so the right eyeball model image displayed was obtained by imaging on Mar. 10, 2018.

As illustrated in FIG. 17, an eyeball model viewed obliquely is displayed in the first eyeball model image display field 326A and an eyeball model of the eyeball model viewed from the side is displayed in the second eyeball model image display field 328. The respective positions Pvv1 to Pvv5 of VV1 to VV5, the respective vectors VC1 to VC5 toward VV1 to VV5, the point Pvvcn determined by the normalized composite vector VCTN from the center C, and the normalized composite vector VCTN are displayed on the eyeball model.

In either the first eyeball model image display field 326A or the second eyeball model image display field 328, when any position out of the respective positions Pvv1 to Pvv5 of VV1 to VV5 or the position of the point Pvven is clicked, respective feature values corresponding to the clicked position are displayed. For example, when the position of the point Pvven is clicked, respective feature values are displayed in the vicinity of the position of the point Pvven. Specifically, a great circle distance GCL between the optic nerve head ONH and the VV center, an angle θ formed when travelling from the macula M position via the optic nerve head ONH position toward the VV center Pvven position, the latitude and longitude of the VV center Pvvon, and the latitudinal distance TL and the longitudinal distance GL of the VV center Pvven are displayed.

Figure 18:
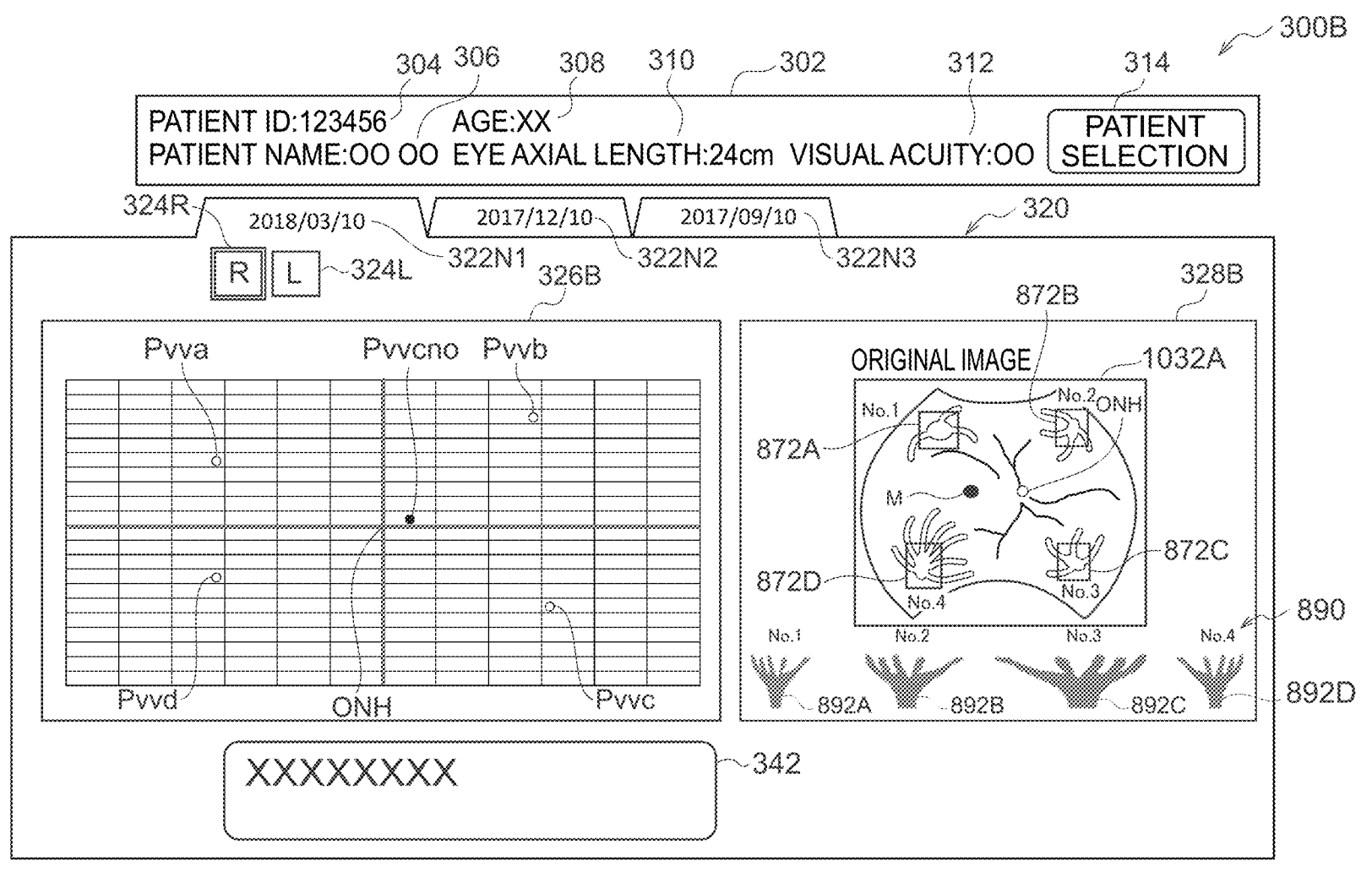

FIG. 18 shows a second display screen 300B for displaying targets and feature values. The second display screen 300B is substantially similar to the first display screen 300A, and so the same reference numerals are appended to similar parts of the display, explanation thereof will be omitted, and explanation will focus on differing parts of the display. Note that switching is performed between the first display screen 300A and the second display screen 300B by using a non-illustrated switching button.

A target position image display field 326B and a target and tomographic image display field 328B are displayed on the second display screen 300B instead of the first eyeball model image display field 326A and the second eyeball model image display field 328.

The example illustrated in FIG. 18 shows an example in which there are four individual VVs detected.

As described previously, the positions on the eyeball are defined in the eyeball model by latitude and longitude, and the latitude and longitude of each of the VVs and the VV center are computed by the feature value computation processing of step 214 of FIG. 6. The positions of each of the VVs and the VV center are displayed in the target position image display field 326B based on the latitude and longitude positional relationships.

The target and tomographic image display field 328B includes an original image display area 1032A and a VV tomographic image display area (OCT image display area 890).

OCT image acquisition regions 872A, 872B, 872C, 872D are displayed overlaid on the original image in the original image display area 1032A. The VV positions are detected at above step 208 of FIG. 6, and in the present exemplary embodiment OCT images are acquired for the OCT image acquisition regions 872A, 872B, 872C, 872D centered on the detected VV positions.

OCT images 892A, 892B, 892C, 892D corresponding to the OCT image acquisition regions 872A, 872B, 872C, 872D are displayed in the OCT image display area 890 by display overlaid on the original image of the original image display area 1032A. The OCT images 892A, 892B, 892C, 892D are displayed, for example, with a shape of the respective vortex vein visualized as a tomographic image by scanning the OCT image acquisition regions 872A, 872B, 872C, 872D. The numbers No. 1, No. 2, No. 3, No. 4 appended at the top of the OCT images 892A, 892B, 892C, 892D correspond to the numbers No. 1, No. 2, No. 3, No. 4 appended to the OCT image acquisition regions 872A, 872B, 872C, 872D. Thus the target and tomographic image display field 328B is able to display the OCT image acquisition regions 872A, 872B, 872C, 872D associated with the OCT images 892A, 892B, 892C, 892D indicating the shape of the visualized vortex veins (or vortex veins and choroidal blood vessels connected to vortex veins).

Images indicating the shapes of the vortex veins are displayed in the OCT image display area 890, however the present exemplary embodiment is not limited thereto. A cross-sectional image of the macula may be displayed in the OCT image display area 890 in cases in which an OCT image of the macula has been acquired, and a cross-sectional image of the optic nerve head may be displayed therein in cases in which an OCT image of the optic nerve head has been acquired.

A non-illustrated display switch button is provided in the OCT image display area 890, and a pull-down menu for switching display of the OCT images 892A, 892B, 892C, 892D is displayed when the display switch button is clicked. Selecting, for example, a 3D polygon, an en-face image, OCT pixels, or a blood flow visualization image or the like from the displayed pull-down menu enables switching of the display of the OCT images 892A, 892B, 892C, 892D.

The present exemplary embodiment as described above enables the VV center to be obtained, and enables diagnostic assistance to be provided to an ophthalmologist by using the VV center.

Moreover, plural feature values to indicate positional relationships between the position of identified sites on the fundus and the position of a center of distribution are computed and displayed in the above exemplary embodiment, enabling further diagnostic assistance using the VV center to be provided to an ophthalmologist. For example, a distance between the optic nerve head and the VV center is computed and displayed as a feature value, enabling an ophthalmologist to understand any displacement (distance) of the VV center from a general position (for example, the position of the optic nerve head OHN).

The exemplary embodiment described above enables the latitude and longitude of a position of a vortex vein to be obtained on an eyeball model spherical surface in which a position of an identified site on the fundus is a position of zero degrees latitude and longitude, and enables a latitudinal distance and a longitudinal distance to be obtained between the position of the identified site and the position of a vortex vein. This enables diagnostic assistance to be provided to an ophthalmologist by using the latitude and longitude of the vortex vein position, and using the latitudinal distance and the longitudinal distance between the identified site position and the vortex vein position.

In the exemplary embodiment described above each of the distances and each of the line segments is a great circle distance, however the technology disclosed herein is not limited thereto. A Euclidean distance (straight line distance) may be computed instead of the great circle distance or as well as the great circle distance.

In the exemplary embodiment described above the VV center is found by the normalized composite vector resulting from normalizing the composite vector obtained by combining the vectors from the VV center to each of the VV positions, however, the technology disclosed herein is not limited thereto.

Namely firstly, for example, the latitude and longitude of each of the VV positions in the eyeball model may be identified, and average values found for the respective latitude and longitude of the VV positions. Then the VV center may be found of the positions (latitude, longitude) on the surface of the eyeball model from the latitude average value and longitude average value that were found.

Secondly, for each point of plural center candidate positions hypothesized as being the VV center on the eyeball model, a total may be found of the respective great circle distances to the VV positions, and identification made using a Monte Carlo method or the like to find the center candidate position having the smallest total great circle distance. Then the center candidate position with the smallest total great circle distance may be taken as the VV center.

Thirdly, rather than utilizing the positions of all of the detected VVs, the positions of VVs that are positioned at probable positions alone from out of detected positions of VVs may be utilized to derive the VV center. For example, only 9 VVs may be used in a case in which 10 VVs have been detected, rather than using all the VVs. The 9 VVs may result from selecting probable VVs obtained from the results of selecting probable VVs, and there may be situations in which there are 8 VVs or 7 VVs. The probable VVs may be selected by eliminating VVs having a distance to a neighboring VV that is less than a specific value, or may be selected by eliminating VVs having a specific value or lower for a number of choroidal blood vessels connected to the VV. In such cases vectors may be computed to the positions of 10 VVs and the vectors to positions of 9 VVs positioned at probable positions combined when combining vectors, or only the vectors to the positions of only the 9 VVs at probable positions computed, and the computed vectors combined.

Although in the above exemplary embodiment the VV center is the subject for computation and display of the feature values, the technology disclosed herein is not limited thereto. For example, a center of distribution of the VVs in the eyeball model (three-dimensional space) may be the subject therefor.

Although the feature values (distance, angle, latitude, longitude, longitudinal distance, latitudinal distance) of the VV center are computed for cases in which the optic nerve head is the datum point (zero degrees latitude and longitude) in the first exemplary embodiment, the technology disclosed herein is not limited thereto. For example, feature values (for example distance, angle, latitude, longitude, longitudinal distance, latitudinal distance) of the VV center may be computed for cases in which the macula M is the datum point (zero degrees latitude and longitude).

Although the positions of each of the points are found using latitude and longitude in the above description, they may be found using polar coordinates.

In the exemplary embodiment described above an example has been described in which a fundus image is acquired by the ophthalmic device 110 with an internal light illumination angle of about 200 degrees. However, the technology disclosed herein is not limited thereto, and the technology disclosed herein may be applied even when the fundus image has been imaged by an ophthalmic device with an internal illumination angle of 100 degrees or less, and may also be applied to a montage image obtained by combining plural fundus images.

Although in the exemplary embodiment described above a fundus image is captured by the ophthalmic device 110 provided with an SLO imaging unit, the technology disclosed herein may also be applied to a configuration in which a fundus image is captured by a fundus camera capable of imaging choroidal blood vessels, or an image is obtained by OCT angiography.

In the exemplary embodiment described above, the management server 140 executes the image processing program. However the technology disclosed herein is not limited thereto. For example, the image processing program may be executed by the ophthalmic device 110, the image viewer 150, or a separate image processing device provided to the network 130. In cases in which the ophthalmic device 110 executes the image processing program, the image processing program is stored in the ROM 16C. In cases in which the image processing program is executed by the image viewer 150, the image processing program is stored in the memory 164 of the image viewer 150. In cases in which the image processing program is executed by the separate image processing device, the image processing program is stored in memory of the separate image processing device.

The exemplary embodiment described above describes an example of the ophthalmic system 100 equipped with the ophthalmic device 110, the eye axial length measurement device 120, the management server 140, and the image viewer 150; however the technology disclosed herein is not limited thereto. For example, as a first example, the eye axial length measurement device 120 may be omitted, and the ophthalmic device 110 may be configured so as to further include the functionality of the eye axial length measurement device 120. Moreover, as a second example, the ophthalmic device 110 may be configured so as to further include the functionality of one or both of the management server 140 and the image viewer 150. For example, the management server 140 may be omitted in cases in which the ophthalmic device 110 includes the functionality of the management server 140. In such cases, the image processing program is executed by the ophthalmic device 110 or the image viewer 150. Moreover, the image viewer 150 may be omitted in cases in which the ophthalmic device 110 includes the functionality of the image viewer 150. As a third example, the management server 140 may be omitted, and the image viewer 150 may be configured so as to execute the functionality of the management server 140.

As long as this does not lead to an internal conflict, there may be one present, or there may be two or more present, of each of the configuration elements (devices and the like) in the present disclosure.

Although explanation has been given in the exemplary embodiment and respective modified examples described above regarding an example in which a computer is employed to implement data processing using a software configuration, the technology disclosed herein is not limited thereto. For example, instead of a software configuration employing a computer, the data processing may be executed solely by a hardware configuration such as a field programmable gate array (FPGA) or an application specific integrated circuit (ASIC). Alternatively, a configuration may be adopted in which some processing out of the data processing is executed by a software configuration, and the remaining processing is executed by a hardware configuration.

Such technology disclosed herein encompasses cases in which the image processing is implemented by a software configuration utilizing a computer, and also cases not implemented by a software configuration utilizing a computer, and encompasses the following technology.

First Technology

An image processing device including a detection section configured to detect positions of plural vortex veins in a fundus image of an examined eye, and a computation section configured to compute a center of distribution of the detected plural vortex vein positions.

Second Technology

An image processing method including a detection section detecting positions of plural vortex veins in a fundus image of an examined eye, and a computation section computing a center of distribution of the detected plural vortex vein positions.

Third Technology

An image processing device including:
a detection section configured to detect positions of plural vortex veins and a position of an optic nerve head in a fundus image of an examined eye;
a projection section configured to project the plural vortex veins and the optic nerve head onto an eyeball surface of an eyeball model;
a generation section configured to generate plural vectors from a center of the eyeball model to positions of the respective vortex veins on the eyeball surface; and
a computation section configured to compute a composite vector combining the plural vectors.

Fourth Technology

An image processing method including:
a detection section detecting positions of plural vortex veins and a position of an optic nerve head in a fundus image of an examined eye;
a projection section projecting the plural vortex veins and the optic nerve head onto an eyeball surface of an eyeball model;
a generation section generating plural vectors from a center of the eyeball model to positions of the respective vortex veins on the eyeball surface; and
a computation section computing a composite vector combining the plural vectors.

The following technology is proposed from the content disclosed above.

Fifth Technology

A computer program product for image processing, the computer program product including a computer-readable storage medium that is not itself a transitory signal, with a program stored on the computer-readable storage medium, and the program causing a computer to execute processing including detecting positions of plural vortex veins in a fundus image of an examined eye, and computing a center of distribution of the detected plural vortex vein positions.

Sixth Technology

A computer program product for image processing, the computer program product including a computer-readable storage medium that is not itself a transitory signal, with a program stored on the computer-readable storage medium, and the program causing a computer to execute processing including:
detecting positions of plural vortex veins and a position of an optic nerve head in a fundus image of an examined eye;

projecting the plural vortex veins and the optic nerve head onto an eyeball surface of an eyeball model;
generating plural vectors from a center of the eyeball model to positions of the respective vortex veins on the eyeball surface; and
computing a composite vector combining the plural vectors.

It must be understood that each image processing described above is merely an example thereof. Obviously redundant steps may be omitted, new steps may be added, and the processing sequence may be swapped around within a range not departing from the spirit of the technology disclosed herein.

All publications, patent applications (including Japanese Patent Application No. 2019-220285) and technical standards mentioned in the present specification are incorporated by reference in the present specification to the same extent as if each individual publication, patent application, or technical standard was specifically and individually indicated to be incorporated by reference.

The invention claimed is:

1. An image processing method performed by a processor, the image processing method comprising:
    detecting positions of a plurality of vortex veins in a fundus image of an examined eye;
    computing a center of distribution of the plurality of detected vortex vein positions;
    wherein the center of distribution computation includes:
        finding a vector from a start point to a position of the vortex vein for each of the plurality of vortex veins; and
        finding a composite vector combining the plurality of vectors;
    wherein the start point is a center point of an eyeball model; and
    each of the plurality of vectors is a vector connecting the center point and a position of a vortex vein projected onto an eyeball surface of the eyeball model.

2. The image processing method of claim 1, wherein the center of distribution computation further includes:
    normalizing the composite vector; and
    computing a point of intersection between the normalized composite vector and the eyeball surface as the center of distribution.

3. The image processing method of claim 1, further comprising computing at least one feature value indicating a positional relationship between a position of an identified site on the examined eye and a position of the center of distribution.

4. The image processing method of claim 3, wherein the at least one feature value is a distance between the center of distribution position and the identified site position.

5. The image processing method of claim 3, wherein the at least one feature value is coordinates of the center of distribution on the eyeball surface of the eyeball model for a case in which a datum point is the identified site position projected onto the eyeball model.

6. The image processing method of claim 5, wherein:
    an arbitrary point on the eyeball surface is expressed by latitude and longitude;
    coordinates of the datum point are zero latitude and zero longitude; and
    coordinates of the center of distribution are determined by a latitude of the center of distribution and a longitude of the center of distribution.

7. The image processing method of claim 3, wherein the identified site is an optic nerve head or a macula.

8. The image processing method of claim 3, wherein:
    the identified site includes:
        a first identified site, and
        a second identified site;
    the first identified site and the second identified site are projected so as to be disposed at zero latitude on the eyeball surface of the eyeball model; and
    the at least one feature value is coordinates of the center of distribution on the eyeball surface for a case in which the first identified site is a datum point.

9. The image processing method of claim 8, wherein:
    the first identified site is an optic nerve head; and
    the second identified site is a macula.

10. An image processing device comprising a memory and a processor coupled to the memory, wherein the processor is configured to:
    detect positions of a plurality of vortex veins in a fundus image of an examined eye; and
    compute a center of distribution of the detected plurality of vortex vein positions.

11. A non-transitory storage medium storing a program that causes a computer to execute processing comprising:
    detecting positions of a plurality of vortex veins in a fundus image of an examined eye;
    computing a center of distribution of the detected plurality of vortex vein positions;
    wherein the center of distribution computation includes:
        finding a vector from a start point to a position of the vortex vein for each of the plurality of vortex veins; and
        finding a composite vector combining the plurality of vectors;
    wherein the start point is a center point of an eyeball model; and
    each of the plurality of vectors is a vector connecting the center point and a position of a vortex vein projected onto an eyeball surface of the eyeball model.

12. An image processing method performed by a processor, the image processing method comprising:
    detecting positions of a plurality of vortex veins and a position of an optic nerve head in a fundus image of an examined eye;
    projecting the plurality of vortex veins and the optic nerve head onto an eyeball surface of an eyeball model;
    generating a plurality of vectors from a center of the eyeball model to positions of the respective vortex veins on the eyeball surface; and
    computing a composite vector combining the plurality of vectors.

13. The image processing method of claim 12, wherein the composite vector is normalized.

14. The image processing method of claim 13, wherein a position of a point of intersection between the normalized composite vector and the eyeball surface is detected as a center of distribution of the plurality of vortex veins.

15. The image processing method of claim 14, further comprising computing a distance between a position of the center of distribution and the position of the optic nerve head.

16. An image processing device comprising a memory and a processor coupled to the memory, wherein the processor is configured to:
    detect positions of a plurality of vortex veins and a position of an optic nerve head in a fundus image of an examined eye;
    project the plurality of vortex veins and the optic nerve head onto an eyeball surface of an eyeball model;

generate a plurality of vectors from a center of the eyeball model to positions of the respective vortex veins on the eyeball surface; and compute a composite vector combining the plurality of vectors.

17. A non-transitory storage medium storing a program causing a computer to execute processing comprising:

detecting positions of a plurality of vortex veins and a position of an optic nerve head in a fundus image of an examined eye;

projecting the plurality of vortex veins and the optic nerve head onto an eyeball surface of an eyeball model;

generating a plurality of vectors from a center of the eyeball model to positions of the respective vortex veins on the eyeball surface; and computing a composite vector combining the plurality of vectors.

\* \* \* \* \*